US011534506B2

(12) United States Patent
Bansal et al.

(10) Patent No.: US 11,534,506 B2
(45) Date of Patent: Dec. 27, 2022

(54) METHODS FOR CELL LABELING AND MEDICAL IMAGING

(71) Applicant: MAYO FOUNDATION FOR MEDICAL EDUCATION AND RESEARCH, Rochester, MN (US)

(72) Inventors: Aditya Bansal, Rochester, MN (US); Timothy R. DeGrado, Rochester, MN (US); Mukesh K. Pandey, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 263 days.

(21) Appl. No.: 15/555,775

(22) PCT Filed: Mar. 7, 2016

(86) PCT No.: PCT/US2016/021188
§ 371 (c)(1),
(2) Date: Sep. 5, 2017

(87) PCT Pub. No.: WO2016/144873
PCT Pub. Date: Sep. 15, 2016

(65) Prior Publication Data
US 2018/0043041 A1    Feb. 15, 2018

Related U.S. Application Data

(60) Provisional application No. 62/129,406, filed on Mar. 6, 2015.

(51) Int. Cl.
*A61K 51/04* (2006.01)
*A61K 51/12* (2006.01)
*A61K 49/10* (2006.01)
*A61K 49/18* (2006.01)

(52) U.S. Cl.
CPC ........ *A61K 51/0478* (2013.01); *A61K 49/103* (2013.01); *A61K 49/106* (2013.01); *A61K 49/1896* (2013.01); *A61K 51/1203* (2013.01)

(58) Field of Classification Search
None
See application file for complete search history.

(56) References Cited

U.S. PATENT DOCUMENTS 5,059,541 A * 10/1991 Fritzberg ........... A61K 51/1093
435/188
8,545,809 B2   10/2013 D'Souza
2006/0035946 A1 * 2/2006 Huang ................. A61K 31/425
514/367

FOREIGN PATENT DOCUMENTS

DE   102012104504      5/2012
WO   2013138696        9/2013
WO   WO-2014164988 A1 * 10/2014 ............. A61K 51/04

OTHER PUBLICATIONS

Vosjan et al. Conjugation and radiolabeling of monoclonal antibodies with zirconium-89 for PET imaging using the bifunctional chelate p-isothiocyanatobenzyl-desferrioxamine. 2010 Nat. Protoc. 5: 739-743. (Year: 2010).*
Miller et al. Synthesis, characterization, and biodistribution of multiple 89Zr-labeled pore-expanded mesoporous silica nanoparticles for PET. 2014 Nanoscale 6: 4928-4935, suppl material. Epub Feb. 21, 2014. (Year: 2014).*
Pérez-Medina et al. A modular labeling strategy for in vivo PET and near-infrared fluorescence imaging of nanoparticle tumor targeting. 2014 J. Nucl. Med. 55: 1706-1711, suppl material. Epub Jul. 24, 2014. (Year: 2014).*
Magnetic types of the elements. From periodictable.com/Properties/A/MagneticType.html. Accessed Mar. 24, 2022. (Year: 2022).*
International Search Report dated Aug. 26, 2016 in connection with PCT/US2016/21188.
Adonai, et al., Ex vivo cell labeling with 64Cu-pyruvaldehyde-bis(N4-methylthiosemicarbazone) for imaging cell trafficking in mice with positron-emission tomography. Proc Nat Acad Sci. 2002;99:3030-5.
Bansal, et al., Novel 89Zr cell labeling approach for PET-based cell trafficking studies. Eur J Nucl Med Mol Imaging Research 2015;5:19.
Borjesson, et al., Radiation dosimetry of Zr-89-labeled chimeric monoclonal antibody U36 as used for immuno-PET in head and neck cancer patients. J Nucl Med. 2009; 50:1828-36.
Borjesson, et al., Performance of immuno-positron emission tomography with zirconium-89-labeled chimeric monoclonal antibody U36 in the detection of lymph node metastases in head and neck cancer patients. Clin Cancer Res. 2006; 12:2133-40.
Brenner, et al., 111In-labeled CD34+ hematopoietic progenitor cells in a rat myocardial infarction model. J Nucl Med. 2004;45:512-8.
Chang, et al., 89Zr-Radiolabeled Trastuzumab Imaging in Orthotopic and Metastatic Breast Tumors. Pharmaceuticals (Basel) 2012;5(1):79-93.
Charoenphun, et al., [89Zr]Oxinate for long-term in vivo cell tracking by positron emission tomography. Eur J Nucl Med Mol Imaging. 2014. [Epub ahead of print].
Daldrup-Link, et al., Cell tracking with gadophrin-2: a bifunctional contrast agent for MR imaging, optical imaging, and fluorescence microscopy. Eur J Nucl Med Mol Imaging 2004;31:1312-21.
De Vries, et al., Guidelines for the labelling of leucocytes with 99mTc-HMPAO. Inflammation/Infection Taskgroup of the European Association of Nuclear Medicine. Eur J Nucl Med Mol Imaging. 2010;37:842-8.
De Vries, University Medical Center Groningen. 89Zr-bevacizumab PET imaging in Patients with Neuroendocrine tumors (NETPET). Clinicaltrials.gov, NCT01338090. https://clinicaltrials.gov/ct2/show/NCT01338090?term=NCT01338090&rank=1.

(Continued)

*Primary Examiner* — Jennifer Lamberski
(74) *Attorney, Agent, or Firm* — Quarles & Brady LLP

(57) ABSTRACT

Methods of ex vivo labeling of a biological material for in vivo imaging, methods of labeling a biological material in vivo, methods for preparing a labeling agent, and methods for in vivo imaging of a subject using a biological material labeled with a labeling agent are disclosed. In one non-limiting example, the biological material is selected from cells and the labeling agent is a $^{89}$Zr-Desferrioxamine-NCS labeling agent.

17 Claims, 19 Drawing Sheets

(56) References Cited

OTHER PUBLICATIONS

Deri, et al., Alternative chelator for $^{89}$Zr radiopharmaceuticals: radiolabeling and evaluation of 3,4,3-(LI-1,2-HOPO). J Med Chem. 2014;57:4849-60.

Deri, et al., PET imaging with 89Zr: from radiochemistry to the clinic. Nucl Med Biol. 2013;40:3-14.

Dijkers, et al., Biodistribution of Zr-89-trastuzumab and PET imaging of HER2-positive lesions in patients with metastatic breast cancer. Clin Pharmacol Ther. 2010; 87:586-92.

Dijkers, et al., Development and characterization of clinical-grade Zr-89-trastuzumab for HER2/neu immunoPET imaging. J Nucl Med. 2009; 50:974-81.

Doyle, et al., Dynamic tracking during intracoronary injection of 18F-FDG-labeled progenitor cell therapy for acute myocardial infarction. J Nucl Med. 2007;48:1708-14.

Fischer, et al., 89Zr, a radiometal nuclide with high potential for molecular imaging with PET: Chemistry, Applications and Remaining Challenges, Molecules, 2013, 18, 6469-6490.

Fischer, et al., Pulmonary passage is a major obstacle for intravenous stem cell delivery: the pulmonary first-pass affect. Stem Cells Dev. 2009;18:683-92.

Gao, et al., The dynamic in vivo distribution of bone marrow-derived mesenchymal stem cells after infusion. Cells Tissues Organs 2001; 169:12-20.

Gaykema, et al., 89Zr-bevacizumab PET imaging in primary breast cancer. J Nucl Med. 2013; 54: 1014-18.

Gildehaus, et al., Impact of indium-111 oxine labelling on viability of human mesenchymal stem cells in vitro, and 3D cell-tracking using SPECT/CT in vivo. Mol Imaging Biol. 2011;13:1204-14.

Glaudemans, et al., Leukocyte and bacteria imaging in prosthetic joint infection. Eur Cell Mater. 2013;25:61-77.

Holland, et al., 89Zr-DFO-J591 for immunoPET of prostate-specific membrane antigen expression in vivo. J Nucl Med. 2010;51:1293-300.

Holland, et al., Standardized methods for the production of high specific-activity zirconium-89. Nucl Med Biol. 2009;36:729-39.

Hughes, Nuclear medicine and infection detection: the relative effectiveness of imaging with 111In-oxine-, 99mTc-HMPAO-, and 99mTc-stannous fluoride colloid-labeled leukocytes and with 67Ga-citrate. J Nucl Med Tech. 2003;31:196-201.

Kassis, et al., Chemotoxicity of indium-111 oxine in mammalian cells. J Nucl Med. 1985;26:187-90.

Keberlem, The Biochemistry of Desferrioxamine and Its Relation to Iron Metabolism. Annals N Y Acad Sci. 1964;119:758-68.

Kuyama, et al., Indium-111 labelled lymphocytes: isotope distribution and cell division. Eur J Nucl Med. 1997;24:488-96.

Meier, et al., Tracking of [18F]FDG-labeled natural killer cells to HER2/neu-positive tumors. Nucl Med Biol. 2008;35:579-88.

Meijs, et al., Production of highly pure no-carrier added 89Zr for the labelling of antibodies with a positron emitter. Appl Radiat Isotopes 1994;45:1143-7.

Naumova, et al., Clinical imaging in regenerative medicine. Nat Biotech. 2014; 32:804-18.

Nguyen, et al., Stem cell imaging: from bench to bedside. Cell stem cell. 2014;14:431-44.

Oosting-Lenstra, University Medical Center Groningen and VHL Family Alliance. Visualizing Vascular Endothelial Growth factor (VEGF) Producing Lesions in Von Hippel-Lindau Disease (VHL image). Clinicaltrials.gov, NCT00970970. https://clinicaltrials.gov/ct2/show/NCT00970970?term=NCT00970970&rank=1.

Oosting-Lenstra, University Medical Center Groningen. VEGF imaging in Renal Cell Carcinoma (Renimage). Clinicaltrials.gov, NCT00831857. https://clinicaltrials.gov/ct2/show/NCT00831857?term=NCT00831857&rank=1.

Pandey, et al., Cyclotron production of 68Ga via the 68Zn (p,n) 68Ga reaction in aqueous solution. Am J Nucl Med Mol Imaging 2014;70: 2308-2312.

Pandey, et al., Production of 89Zr via the 89Y(p,n)89Zr reaction in aqueous solution: effect of solution composition on in-target chemistry. Nucl Med Biol. 2014;41:309-16.

Pandey, et al., Synthesis and Preliminary Evaluation of N-(16-18F-fluorohexadecanoyl)ethanolamine (18F-FHEA) as a PET Probe of N-Acylethanolamine Metabolism in Mouse Brain. ACS Chem Neurosci, 2014; 5(9):793-802.

Pellegrino, et al., Inflammation and infection: imaging properties of 18F-FDG-labeled white blood cells versus 18F-FDG. J Nucl Med. 2005; 46:1522-30.

Perk, et al., p-Isothiocyanatobenxyl-desferrioxamine: a new biofunctional chelate for facile radiolabeling of monoclonal antibodies with zirconium-89 for immune-PET imaging, Eur J Nucl Med Mol Imaging, 2010, 37:250-259.

Rizvi, et al., Biodistribution, radiation dosimetry and scouting of Y-90-ibritumomab tiuxetan therapy in patients with relapsed B-cell non-Hodgkin's lymphoma using Zr-89-ibritumomab tiuxetan and PET. Eur J Nucl Med Mol Imaging. 2012; 39:512-20.

Roca, et al., Guidelines for the labelling of leucocytes with (111)In-oxine. Inflammation/Infection Taskgroup of the European Association of Nuclear Medicine. Eur J Nucl Med Mol Imaging. 2010;37:835-41.

Ruysscher, Maastricht Radiation Oncology and VU University Medical Center. Non-invasive Imaging of Cetuximab-89Zr uptake with PET: A Phase I Trial in Stage IV Cancer Patients. Clinicaltrials.gov, NCT00691548. https://clinicaltrials.gov/ct2/show/NCT00691548?term=NCT00691548&rank=1.

Sadeghi, et al., Targetry of Y2O3 on a copper substrate for the non-carrier-added 89Zr production via 89Y(p, n) 89Zr reaction. Kerntechnik. 2010;75:298-302.

Sato, et al., Cell labeling using Zr-89—comparison with In-111 oxine. Proceedings World Molecular Imaging Congress, Savannah, GA, 2013, 2013: p. P533.

Schrepfer, et al., Stem cell transplantation: the lung barrier. Transplant Proc. 2007;39:573-6.

Schroder, University Medical Center Groningen. VEGF Early Imaging for Breast Cancer. Clinicaltrials.gov, NCT00991978. https://clinicaltrials.gov/ct2/show/NCT00991978?term=NCT00991978&rank=1.

Stojanov, et al., [18F]FDG labeling of neural stem cells for in vivo cell tracking with positron emission tomography: inhibition of tracer release by phloretin. Mol Imaging. 2012; 11:1-12.

Takagai, et al., Adsorption behaviors of high-valence metal ions on desferrioxamine B immobilization nylon 6,6 chelate fiber under highly acidic conditions. J Colloid Interface Sci. 2007;313:359-62.

Yang, et al., Tracking and therapeutic value of human adipose tissue-derived mesenchymal stem cell transplantation in reducing venous neointimal hyperplasia associated with arteriovenous fistula, Radiology, 2016, 279(2).

Zhang, et al., 18F-FDG cell labeling may underestimate transplanted cell homing: more accurate, efficient, and stable cell labeling with hexadecyl-4-[18F]fluorobenzoate for in vivo tracking of transplanted human progenitor cells by positron emission tomography. Cell Transplant. 2012; 21:1821-35.

Tarantal, et al., Radiolabeling human peripheral blood stem cells for positron emission tomography (PET) imaging in young rhesus monkeys. PloS one. 2013;8:e77148.

Terrovitis, et al., Noninvasive quantification and optimization of acute cell retention by in vivo positron emission tomography after intramyocardial cardiac-derived stem cell delivery. J Am Coll Cardiol. 2009;54:1619-26.

Van de Watering, et al., Zirconium-89 Labeled Antibodies: A New Tool for Molecular Imaging in Cancer Patients. BioMed Research International 2014, article ID 203601, 13.

Verel, et al., 89Zr immuno-PET: comprehensive procedures for the production of 89Zr-labeled monoclonal antibodies. J Nucl Med 2003;44:1271-81.

Vosjan, et al., Conjugation and radiolabeling of monoclonal antibodies with zirconium-89 for PET imaging using the bifunctional chelate p-isothiocyanatobenzyl-desferrioxamine. Nat Protoc. 2010;5:739-43.

Butcher, E.C., et al. "Direct fluorescent labeling of cells with fluorescein or rhodamine isothiocyanate. I. Technical aspects." Journal of immunological methods 37.2 (1980): 97-108.

(56) References Cited

OTHER PUBLICATIONS

European Search Report for PCT/US2016/2016021188, dated Dec. 17, 2018, 10 pages.
European Search Report for PCT/US2016/2016021188, dated Sep. 14, 2018, 12 pages.
Lee, J., et al. "A steroid-conjugated contrast agent for magnetic resonance imaging of cell signaling." Journal of the American Chemical Society 127.38 (2005): 13164-13166.
Quan, G.B. et al. "In vivo circulation of mouse red blood cells frozen in the presence of dextran and glucose." Cryobiology 61.1 (2010): 10-16.
Zeglis, B.M., et al. "The bioconjugation and radiosynthesis of 89Zr-DFO-labeled antibodies." Journal of visualized experiments: JoVE 96 (2015).

* cited by examiner

MOI:2500
2.5 X 10^5 293T cells
with 6.3 X 10^8 viral
particles

MOI:10,000
2.5 X 10^5 293T cells
with 2.5 X 10^9 viral
particles

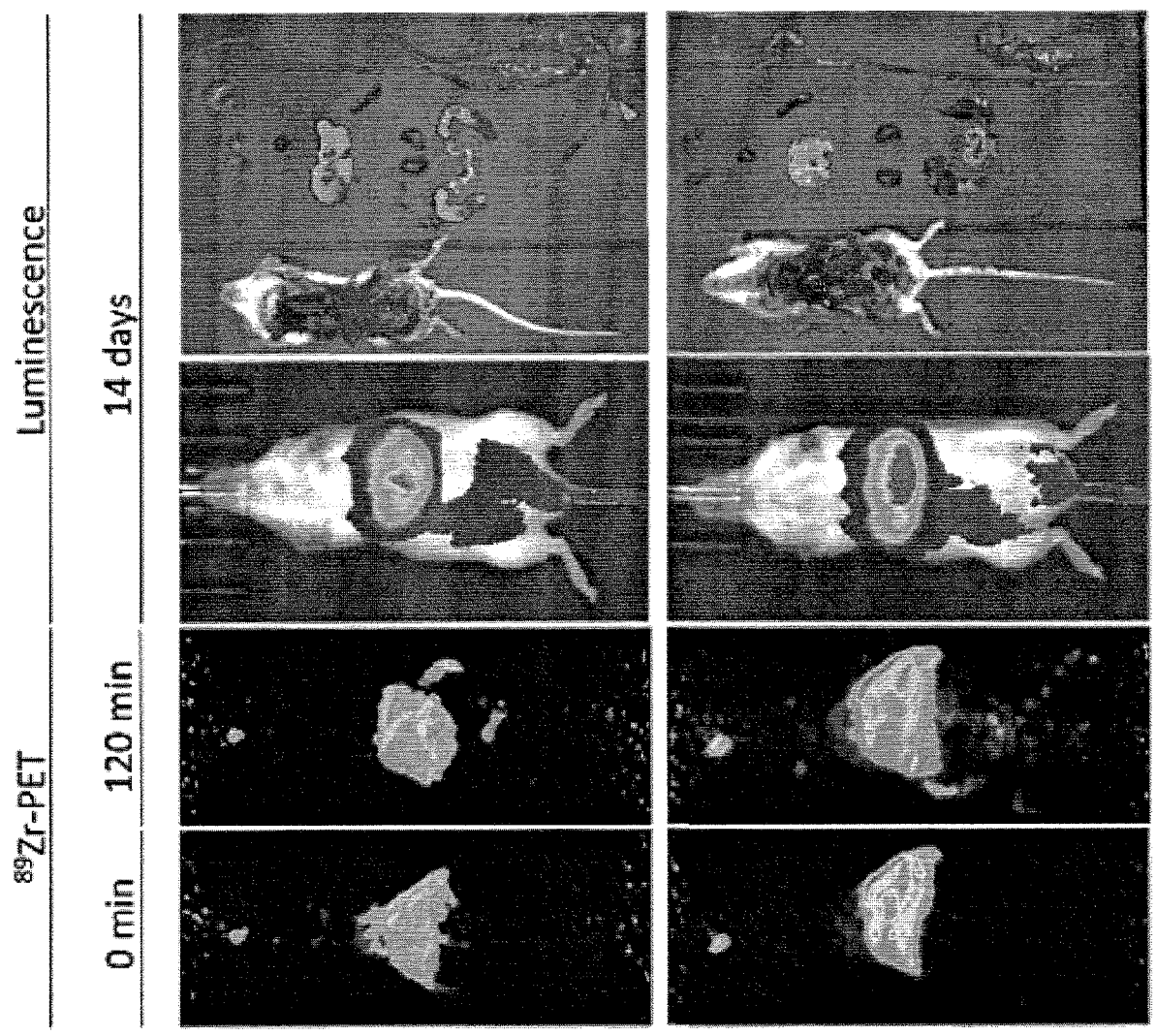

METHODS FOR CELL LABELING AND MEDICAL IMAGING

CROSS-REFERENCE TO RELATED APPLICATIONS

This application represents the national stage entry of PCT International Application No. PCT/US2016/021188 filed on Mar. 7, 2016 and claims priority to U.S. Provisional Patent Application Ser. No. 62/129,406 filed on Mar. 6, 2015, the contents of which are hereby incorporated by reference as if set forth in their entirety herein.

STATEMENT REGARDING FEDERALLY SPONSORED RESEARCH

Not Applicable.

BACKGROUND OF THE INVENTION

1. Field of the Invention

This invention relates to methods of ex vivo labeling of a biological material for in vivo imaging, methods of labeling a biological material in vivo, methods for preparing a labeling agent, and methods for in vivo imaging of a subject using a biological material labeled with a labeling agent. In one non-limiting example, the biological material is selected from cells.

2. Description of the Related Art

A number of radioisotopic cell labeling methods have traditionally been used for single-photon emission computerized tomography (SPECT) and positron emission tomography (PET) imaging based cell tracking [Ref. 1]. However, a PET-based approach would offer superior quantification and imaging sensitivity characteristics over a SPECT-based approach, which are critical for tracking of small numbers of administered cells [Ref. 1]. In this regard, $^{89}$Zr has emerged as an attractive PET radionuclide for cell labeling applications due to its high spatial resolution and 78.4 hour half-life that may allow monitoring of administered cells up to a 2-3 week period.

Traditionally, cell-labeling strategies have relied on transport of a radiometal ($^{111}$In, $^{99m}$Tc, $^{64}$Cu, $^{89}$Zr) into cells in conjunction with oxine, hexamethylpropyleneamine oxime (HMPAO), pyruvaldehyde-bis(N4-methylthiosemicarbazone) (PTSM) or protamine sulfate [Ref. 1]. After entry into the cell, the radiometal dissociates and binds to a variety of intracellular biomolecules. The major drawback of this approach is that appreciable efflux of sequestered radioactivity is observed post-labeling (See Table 1).

TABLE 1

Present Direct Radioisotopic Cell Labeling Methods

| Isotope-Compound/ $T_{1/2}$ | Cells labeled | Labeling and imaging characteristics | Ref. |
|---|---|---|---|
| $^{111}$In-oxine/ 67.4 hours | Leukocytes Lymphocytes HPCs* | ~80% cell labeling yield in 30 minutes Significant efflux rate reported in lymphocytes (~70% effluxed in 24 hours) and HPCs (~75% effluxed in 96 hours) Suboptimal image quality and sensitivity | [2-6] |
| $^{64}$Cu-PTSM/ 12.7 hours | C6 glioma cells | 70-85% cell labeling yield in 5 hours Significant efflux rate from cells (~80% effluxed in 24 hours h) | [7] |
| $^{64}$Cu-TETA- or $^{89}$Zr-DFO-antiCD45/ 12.7 hours ($^{64}$Cu) 78.4 hours ($^{89}$Zr) | hPBSCs# | Binds to only CD45 membrane protein expressing cells Approach was sub-optimal possibly due to insufficient CD45 molecules on the plasma membrane of stem cells | [8] |
| $^{89}$Zr-oxine/ 78.4 hours | myeloma cells and natural killer cells | ~32% cell labeling yield in 30 minutes Significant efflux rate reported for myeloma cells (29% effluxed in 24 hours) and natural killer cells (70-80% effluxed in 7 days) Loss of cell viability possibly due to oxine exposure | [9-10] |
| $^{89}$Zr-protamine sulfate/ 78.4 hours | dendritic cells and T lymphocytes | ~34% cell labeling yield (dendritic cells) in 30 minutes ~12% cell labeling yield (T lymphocytes) in 30 minutes Weakly binds to non-specific intracellular biomolecules Efflux rate not reported | [11] |

*HPCs—Hematopoietic Progenitor Cells,
hPBSCs—human Peripheral Blood Stem Cells

The extent of efflux has been as high as 70-80% in 24-96 hours as reported for $^{111}$In-oxine labeled lymphocytes [Ref. 5], $^{111}$In-oxine labeled hematopoietic progenitor cells [Ref. 4], and $^{64}$Cu-PTSM labeled C6 glioma cells [Ref. 7]. Recently, $^{89}$Zr-oxine has been reported as a labeling molecule but like $^{111}$In-oxine, it also undergoes efflux (10-29% at 24 hours in macrophages, breast cancer cells, and myeloma cells [Ref. 9] and 70-80% at 24 hours in natural killer cells [Ref. 10]). Efflux of radiolabel significantly limits monitoring cell trafficking over longer observational periods. Cells have also been labeled with $^{18}$F-FDG [12-16] ($T_{1/2}$=109.8 minutes), $^{99m}$Tc-HMPAO [17] ($T_{1/2}$=6 hours) and $^{64}$Cu-labeled anti-CD45 [Ref. 8] ($T_{1/2}$=12.7 hours), but the short half-lives of these radioisotopes limit their utility for cell tracking to shorter observational periods. An alternative antibody based stem cell labeling method employed $^{89}$Zr-labeled anti-CD45 for ex vivo labeling of stem cells expressing CD45 membrane protein. However, this radiotracer yielded poor in vivo imaging characteristics, possibly due to insufficient CD45 molecules on the plasma membrane of stem cells [Ref. 8].

Therefore, with the growth of interest in cell-based therapies, there is a need to develop more sensitive, robust and quantitative imaging methods for in vivo tracking of living cells.

SUMMARY OF THE INVENTION

In one aspect, the invention provides a method of ex vivo labeling of a cell for in vivo imaging. The method includes the step of contacting a cell ex vivo with a labeling agent such that the cell becomes labeled for in vivo imaging, wherein the labeling agent comprises a chelating moiety, a conjugation moiety, and at least one of (i) a radionuclide and (ii) a paramagnetic metal ion or compound. The labeling agent may include a radionuclide, or a paramagnetic metal ion or compound, or both a radionuclide and a paramagnetic metal ion or compound.

In another aspect, the invention provides a method of labeling a cell in vivo. The method includes the step of administering to a subject a labeling agent thereby labeling a cell in vivo, wherein the labeling agent does not include an antibody, and wherein the labeling agent comprises a chelating moiety, a conjugation moiety, and at least one of (i) a radionuclide and (ii) a paramagnetic metal ion or compound. The labeling agent may include a radionuclide, or a paramagnetic metal ion or compound, or both a radionuclide and a paramagnetic metal ion or compound.

In another aspect, the invention provides a method of ex vivo labeling of a biological material for in vivo imaging. The method includes the step of contacting a biological material ex vivo with a labeling agent such that the biological material becomes labeled for in vivo imaging, wherein labeling agent comprises a chelating moiety, a conjugation moiety, and at least one of (i) a radionuclide and (ii) a paramagnetic metal ion or compound, and wherein the biological material is selected from cells, liposomes, DNA aptamers, RNA aptamers, viruses, nanoparticles, microorganisms, antibodies, proteins, peptides, scaffolds, polymers, and nucleic acids. The labeling agent may include a radionuclide, or a paramagnetic metal ion or compound, or both a radionuclide and a paramagnetic metal ion or compound.

In another aspect, the invention provides a method of labeling a biological material in vivo. The method includes the step of administering to a subject a labeling agent thereby labeling a biological material in vivo, wherein the labeling agent comprises a chelating moiety, a conjugation moiety, and at least one of (i) a radionuclide and (ii) a paramagnetic metal ion or compound, and wherein the biological material is selected from cells, liposomes, DNA aptamers, RNA aptamers, viruses, nanoparticles, microorganisms, proteins, peptides, scaffolds, polymers, and nucleic acids. The labeling agent may include a radionuclide, or a paramagnetic metal ion or compound, or both a radionuclide and a paramagnetic metal ion or compound.

In the foregoing methods of the invention, the chelating moiety may be a hydroxamic acid group, and preferably, the hydroxamic acid group is a desferrioxamine group. The conjugation moiety may include an isothiocyanate group. The conjugation moiety may include a benzyl group, or a maleimide group, or an NHS ester group, or a combination thereof. The labeling agent may be $^{89}$Zr-isothiocyanato-benzyl-desferrioxamine.

In the foregoing methods of the invention, the radionuclide may be selected from the group consisting of $^{11}$C, $^{13}$N, $^{15}$O, $^{18}$F, $^{34m}$Cl, $^{38}$K, $^{45}$Ti, $^{51}$Mn, $^{52}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{99m}$Tc, $^{110m}$In, $^{111}$In, $^{118}$Sb, $^{120}$I, $^{121}$I, $^{122}$I, $^{123}$I, and $^{124}$I. The radionuclide may be a positron emitter, such as $^{89}$Zr. The paramagnetic metal ion may be selected from Gd$^{+3}$, Fe$^{+3}$, Mn$^{+2}$, and Y$^{+3}$. There are a number of chelators that may be used to chelate the paramagnetic metal ion (e.g., Gd$^{+3}$, Fe$^{+3}$, Mn$^{+2}$, and Y$^{+3}$). Non-limiting example chelators for the paramagnetic metal ion are diethylenetriaminepentaacetic acid (DTPA), ethylenediaminetetraacetic acid (EDTA), 1,4,7,10-tetraazacyclododecane-1,4,7,10-tetraacetic acid (DOTA), and 1,4,7-triazacyclononane-triacetic acid (NOTA). The paramagnetic compound may be compounds including $^{19}$F, such as a perfluorocarbon.

The biological material may be cells selected from microorganisms, blood-derived cells, cancer cells, stem cells, and dendritic cells. The biological material may be selected from stem cells. The biological material may be selected from viruses.

In another aspect, the invention provides a labeling agent comprising a chelating moiety, a conjugation moiety, and at least one of (i) a radionuclide and (ii) a paramagnetic metal ion or compound, wherein the chelating moiety includes a hydroxamic acid group and the conjugation moiety includes an isothiocyanate group, and wherein the labeling agent is in a reactive form suitable for labeling a biological material selected from cells, liposomes, DNA aptamers, RNA aptamers, viruses, nanoparticles, microorganisms, antibodies, proteins, peptides, scaffolds, polymers, and nucleic acids.

In the labeling agent, the chelating moiety may be a hydroxamic acid group, and preferably, the hydroxamic acid group is a desferrioxamine group. The conjugation moiety may include an isothiocyanate group. The conjugation moiety may include a benzyl group, or a maleimide group, or an NHS ester group, or a combination thereof. The labeling agent may be $^{89}$Zr-isothiocyanato-benzyl-desferrioxamine. The radionuclide may be selected from the group consisting of $^{11}$C, $^{13}$N, $^{15}$O, $^{18}$F, $^{34m}$Cl, $^{38}$K, $^{45}$Ti, $^{51}$Mn, $^{52}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{99m}$Tc, $^{110m}$In, $^{111}$In, $^{118}$Sb, $^{120}$I, $^{121}$I, $^{122}$I, $^{123}$I, and $^{124}$I. The radionuclide may be a positron emitter, such as $^{89}$Zr. The paramagnetic metal ion may be selected from Gd$^{+3}$, Fe$^{+3}$, Mn$^{+2}$, and Y$^{+3}$. The paramagnetic compound may be compounds including $^{19}$F, such as a perfluorocarbon. The biological material may be cells that are selected from microorganisms, blood-derived cells, cancer cells, stem cells, and dendritic cells. The biological material may be selected from stem cells. The biological material may be selected from viruses.

In another aspect, the invention provides a method for preparing a labeling agent. The method includes the steps of: (a) providing a compound including a chelating moiety and a conjugation moiety; and (b) mixing the compound with at least one of (i) a radionuclide and (ii) a paramagnetic metal ion or compound to create the labeling agent before reacting the compound with an additional moiety, wherein the chelating moiety includes a hydroxamic acid group and the conjugation moiety includes an isothiocyanate group.

In the method for preparing a labeling agent, the additional moiety may be a lysine residue. The additional moiety may be a functional group of at least one of a liposome, DNA aptamer, RNA aptamer, a virus, nanoparticles, microorganisms, antibodies, proteins, peptides, scaffolds, polymers, and nucleic acids. The additional moiety may be a functional group of a stem cell. The additional moiety may be a functional group of a virus. The chelating moiety may be a desferrioxamine group. The conjugation moiety may include a benzyl group. The labeling agent can be a $^{89}$Zr-isothiocyanato-benzyl-desferrioxamine.

In another aspect, the invention provides a method for in vivo imaging of a subject. The method includes the steps of: (a) administering to the subject a biological material labeled with a labeling agent comprising a chelating moiety, a conjugation moiety, and at least one of (i) a radionuclide and (ii) a paramagnetic metal ion or compound; (b) waiting a time sufficient to allow the labeled cells to accumulate at a tissue site to be imaged; and (c) imaging the tissues with a non-invasive imaging technique such as positron emission tomography imaging, wherein the biological material is selected from cells, liposomes, DNA aptamers, RNA aptamers, viruses, nanoparticles, microorganisms, proteins, peptides, scaffolds, polymers, and nucleic acids.

In another aspect, the invention provides a method of imaging a subject by emission tomography. The method comprises: (a) administering to the subject a biological material labeled with a labeling agent comprising a chelating moiety, a conjugation moiety, and at least one of (i) a radionuclide and (ii) a paramagnetic metal ion or compound; (b) using a plurality of detectors to detect gamma rays emitted from the subject and to communicate signals corresponding to the detected gamma rays; and (c) reconstructing from the signals a series of medical images of a region of interest of the subject, wherein the biological material is selected from cells, liposomes, DNA aptamers, RNA aptamers, viruses, nanoparticles, microorganisms, proteins, peptides, scaffolds, polymers, and nucleic acids.

In another aspect, the invention provides an imaging method comprising acquiring an image of a subject to whom a detectable amount of a biological material labeled with a labeling agent comprising a chelating moiety, a conjugation moiety, and at least one of (i) a radionuclide and (ii) a paramagnetic metal ion or compound has been administered, wherein the biological material is selected from cells, liposomes, DNA aptamers, RNA aptamers, viruses, nanoparticles, microorganisms, proteins, peptides, scaffolds, polymers, and nucleic acids. In the method, an image is acquired using positron emission tomography imaging, positron emission tomography with computed tomography imaging, or positron emission tomography with magnetic resonance imaging.

In another aspect, the invention provides an emission tomography system for acquiring a series of medical images of a subject during an imaging process using a radiotracer. The system comprises: a plurality of detectors configured to be arranged about the subject to acquire gamma rays emitted from the subject over a time period relative to an administration of the radiotracer to the subject and communicate signals corresponding to acquired gamma rays; a data processing system configured to receive the signals from the plurality of detectors; and a reconstruction system configured to receive the signals from the data processing system and reconstruct therefrom a series of medical images of the subject. The radiotracer comprises a biological material labeled with a labeling agent comprising a chelating moiety, a conjugation moiety, and at least one of (i) a radionuclide and (ii) a paramagnetic metal ion or compound. The biological material is selected from cells, liposomes, DNA aptamers, RNA aptamers, viruses, nanoparticles, microorganisms, proteins, peptides, scaffolds, polymers, and nucleic acids.

In the imaging methods and systems of the invention, the image may be acquired using positron emission tomography imaging, positron emission tomography with computed tomography imaging, or positron emission tomography with magnetic resonance imaging. The biological material may be selected from cells. The chelating moiety may be a hydroxamic acid group. The hydroxamic acid group may be a desferrioxamine group. The conjugation moiety may include an isothiocyanate group, a benzyl group, or a maleimide group, or an NHS ester group, or a combination thereof. The cells may be selected from microorganisms, blood-derived cells, cancer cells, stem cells, and dendritic cells. The biological material may be selected from stem cells. The biological material may be selected from viruses.

In the imaging methods and systems of the invention, the radionuclide may be selected from the group consisting of $^{11}C$, $^{13}N$, $^{15}O$, $^{18}F$, $^{34m}Cl$, $^{38}K$, $^{45}Ti$, $^{51}Mn$, $^{52}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{99m}Tc$, $^{110m}In$, $^{111}In$, $^{118}Sb$, $^{120}I$, $^{121}I$, $^{122}I$, $^{123}I$, and $^{124}I$. The radionuclide may be a positron emitter, such as $^{89}Zr$. The paramagnetic metal ion may be selected $Gd^{+3}$, $Fe^{+3}$, $Mn^{+2}$, and $Y^{+3}$. The labeling agent may include a metal ion that is both a positron emitter and paramagnetic. For example, $^{52}Mn$ is a positron emitter which has a half-life similar to $^{89}Zr$ (Half-life: 3.26 days). Also, $^{52}Mn$ is paramagnetic which allows for a dual modality cell labeling reagent (e.g., positron emission tomography with magnetic resonance imaging). The paramagnetic compound may be compounds including $^{19}F$, such as a perfluorocarbon.

The imaging methods and systems and labeling agents of the invention can provide for detection of the radiolabeled biological material in vivo for a time period of one or more days. For example, a detection time period of the radiolabeled biological material in vivo can be beyond 24 hours, or beyond 2 days, or beyond 3 days, or beyond 4 days, or beyond 5 days, or beyond 7 days, or beyond 9 days, or beyond 13 days, or beyond 21 days.

The invention also provides a novel cell labeling strategy that covalently binds a $^{89}Zr$-Desferrioxamine-labeling agent to cell surface proteins independent of cell type.

It is therefore an advantage of the invention to provide methods of ex vivo labeling of a cell for in vivo imaging, methods of labeling a cell in vivo, methods for preparing a labeling agent, and methods for in vivo imaging of a subject using a biological material labeled with a labeling agent.

It is another advantage of the method that Zr-89 DBN may act as a general Zr-89 labeling synthon. It can be produced at a centralized facility and shipped to various sites and labs that need to perform labeling of biological materials such as, without limitation, cells, liposomes, DNA aptamers, RNA aptamers, viruses, nanoparticles, microorganisms, antibodies, proteins, peptides, scaffolds, polymers, and nucleic acids.

These and other features, aspects, and advantages of the present invention will become better understood upon consideration of the following detailed description, drawings and appended claims.

BRIEF DESCRIPTION OF THE DRAWINGS

In FIG. 12B, SUV=standardized uptake value.

FIG. 14 shows representative serial PET images and bioluminescence images showing biodistribution and transfection profile of $^{89}$Zr-labeled AAVs.

DETAILED DESCRIPTION OF THE INVENTION

For cell-based therapies, early engraftment period of 2-5 weeks post cell delivery is the most critical time period. Therefore, imaging based methods should be robust over this time frame to allow evaluation of various interventions for improving cell engraftment. The ability to monitor cells in vivo beyond 24 hours is also of high importance for evaluation of infection using radiolabeled leukocytes. Conventional infection imaging protocols perform imaging at 1 hour, 4 hours and 24 hours post-injection to differentiate between inflammatory, acute infection and chronic infection loci, however in some patients, 48 hours are necessary for reliable detection of infected lesions.

In one non-limiting example embodiment, a method of this disclosure may employ a two-step method (see FIG. 1): (1) preparation of $^{89}$Zr-labeled p-isothiocyanato-benzyl-desferrioxamine ($^{89}$Zr-DBN) and (2) random labeling of primary amines of cell surface proteins with $^{89}$Zr-DBN. This labeling strategy has been evaluated in cell types such as mouse melanoma cells (mMCs), human mesenchymal stem cells (hMSCs) and mouse dendritic cells (mDCs). The labeled cells were evaluated for 7 days post-labeling for label retention and probable changes in cell proliferation, cell viability and degree of apoptosis in radiolabeled cells as compared to their unlabeled counterparts. Out of these, labeled hMSCs were further tested for imaging characteristics and stability of radiolabel in an in vivo mouse model.

Improvement to the stability of the $^{89}$Zr radiolabel on cells can be seen when using $^{89}$Zr-desferrioxamine-NCS ($^{89}$Zr-DBN) as a labeling entity capable of forming covalent bonds with primary amines of cell surface protein as described herein. Because all cells express cell surface protein with exposed lysine residues and other primary amines, labeling with $^{89}$Zr-DBN also provides a general labeling method to label a broad array of cells.

$^{89}$Zr-DBN cellular-labeling exploits both the strength of chelation of $^{89}$Zr by desferrioxamine (DFO) with three hydroxamate groups (qualitative Zr-binding constant=~1031) as well as the inherent biostability of the thiourea bond that conjugates—NCS group in $^{89}$Zr-DBN to primary amines of a protein. One could also replace the conjugation moiety from the NCS group of Zr-89 DBN to a maleimide group that would then conjugate thiols on cell surface protein. Alternatively, an NHS ester group could be employed to target primary amines, just like the NCS group of $^{89}$Zr-desferrioxamine-NCS. Generally, an activated group with amine, thiol or hydroxyl moiety could react with the NCS group.

The generality of the labeling target, along with the multiplicity of primary amines available on the cell surface, also avoids the specific targeting of highly sensitive processes that might affect cellular function or viability.

Figure 1:
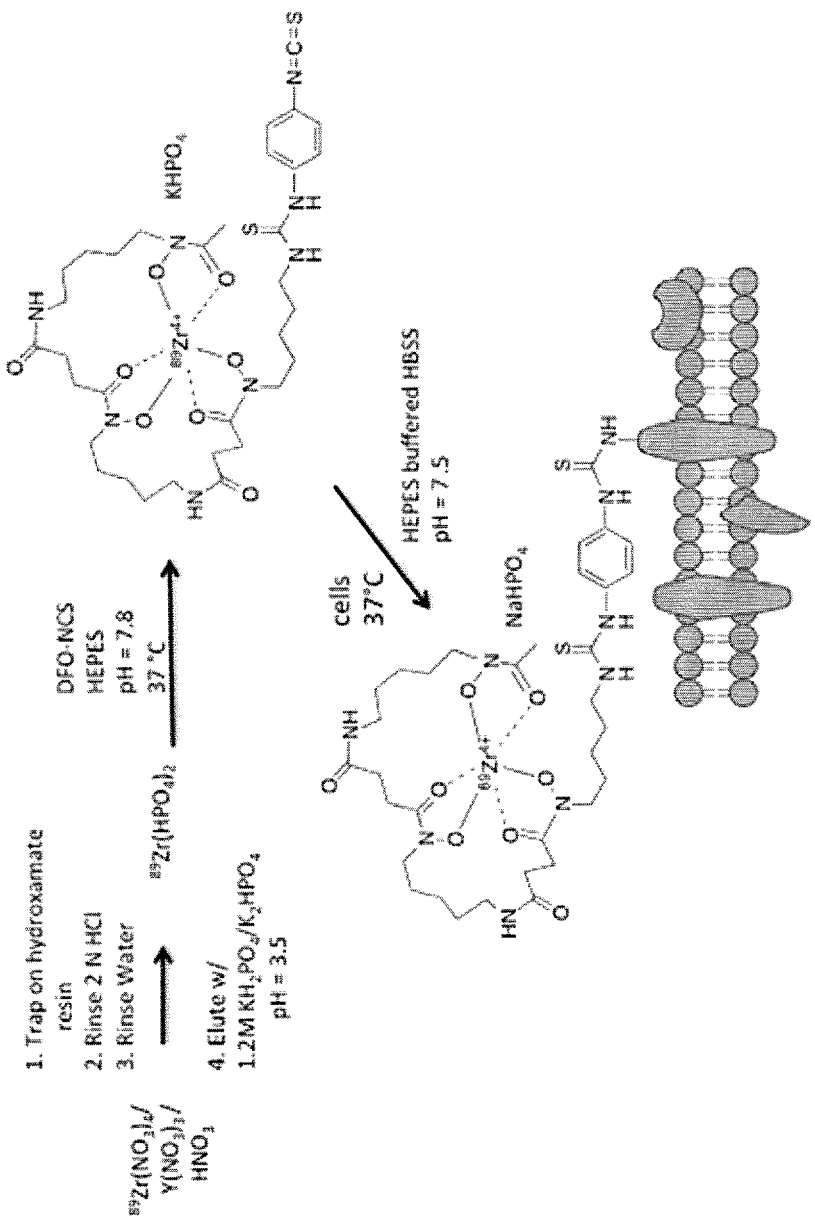
FIG. 1 is a scheme for synthesis of $^{89}Zr$-DBN and cell labeling.

A method for labeling cells with $^{89}$Zr-DBN can be seen in FIG. 1. The method employs two steps: (i) preparation of $^{89}$Zr-labeled p-isothiocyanato-benzyl-desferrioxamine ($^{89}$Zr-DBN) and (ii) random labeling of primary amines of cell surface proteins with $^{89}$Zr-DBN.

In another non-limiting example embodiment, a method of this disclosure may employ a two-step method (see FIG. 1): (1) preparation of $^{89}$Zr-labeled p-isothiocyanato-benzyl-desferrioxamine ($^{89}$Zr-DBN) and (2) random labeling of viruses with $^{89}$Zr-DBN. This labeling strategy has been evaluated in viruses such as AAV1, AAV2, AAv8 and AAV9.

Figure 2:
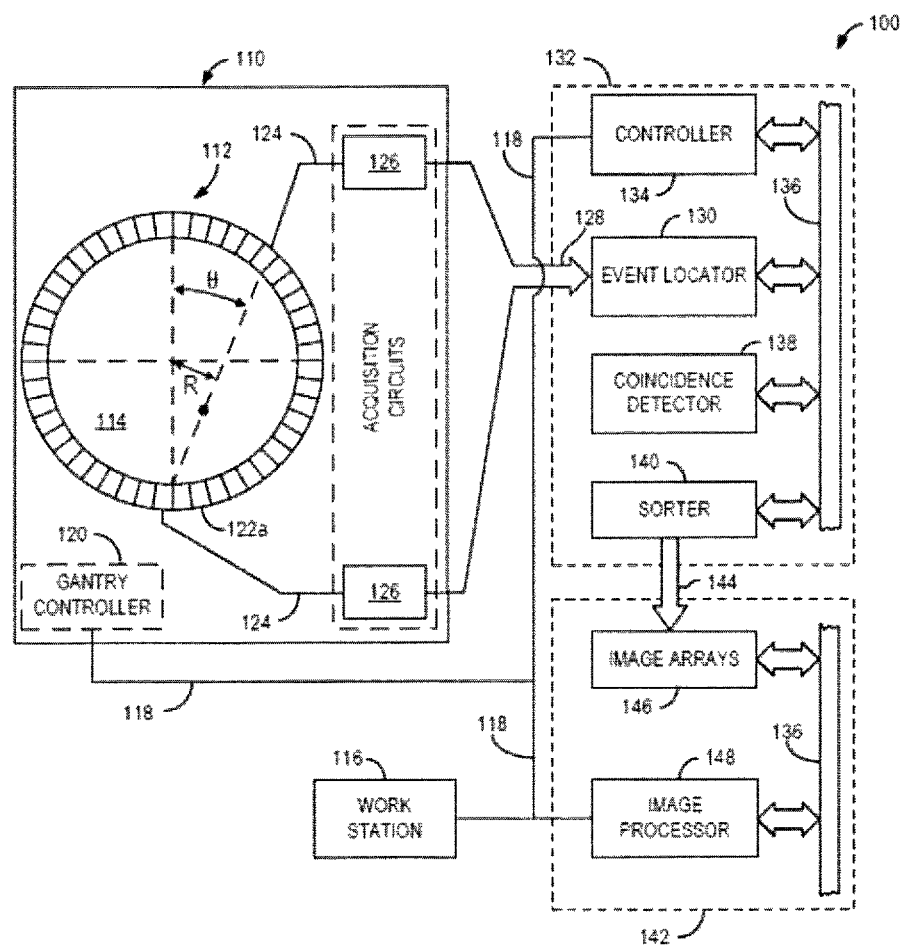
FIG. 2 is a schematic of a positron emission tomography (PET) system.

Referring now to FIG. 2, a PET system 100 that can be used with the labeled cells of the present invention comprises an imaging hardware system 110 that includes a detector ring assembly 112 about a central axis, or bore 114. An operator work station 116 including a commercially-available processor running a commercially-available operating system communicates through a communications link 118 with a gantry controller 120 to control operation of the imaging hardware system 110.

The detector ring assembly 112 is formed of a multitude of radiation detector units 122 that produce a signal responsive to detection of a photon on communications line 124 when an event occurs. A set of acquisition circuits 126 receive the signals and produce signals indicating the event coordinates (x, y) and the total energy associated with the photons that caused the event. These signals are sent through a cable 128 to an event locator circuit 130. Each acquisition circuit 126 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 130 in some implementations, form part of a data acquisition processing system 132 that periodically samples the signals produced by the acquisition circuits 126. The data acquisition processing system 132 includes a general controller 134 that controls communications on a backplane bus 136 and on the general communications network 118. The event locator circuits 130 assemble the information regarding each valid event into a set of numbers that indicate precisely when the event took place and the position in which the event was detected. This event data packet is conveyed to a coincidence detector 138 that is also part of the data acquisition processing system 132.

The coincidence detector 138 accepts the event data packets from the event locator circuit 130 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 114. Events that cannot be paired are discarded from consideration by the coincidence detector 138, but coincident event pairs are located and recorded as a coincidence data packet. These coincidence data packets are provided to a sorter 140. The function of the sorter in many traditional PET imaging systems is to receive the coincidence data packets and generate memory addresses from the coincidence data packets for the efficient storage of the coincidence data. In that context, the set of all projection rays that point in the same direction (θ) and pass through the scanner's field of view (FOV) is a complete projection, or "view". The distance (R) between a particular projection ray and the center of the FOV locates that projection ray within the FOV. The sorter 140 counts all of the events that occur on a given projection ray (R, θ) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each projection ray (R, θ) and organizes them into an image data array.

The sorter 140 provides image datasets to an image processing/reconstruction system 142, for example, by way of a communications link 144 to be stored in an image array 146. The image arrays 146 hold the respective datasets for access by an image processor 148 that reconstructs images. The image processing/reconstruction system 142 may communicate with and/or be integrated with the work station 116 or other remote work stations.

The PET system 100 provides an example emission tomography system for acquiring a series of medical images of a subject during an imaging process after administering a pharmaceutically acceptable composition including labeled cells as described herein. The system includes a plurality of detectors configured to be arranged about the subject to acquire gamma rays emitted from the subject over a time period relative to an administration of the composition to the subject and communicate signals corresponding to acquired gamma rays. The system also includes a reconstruction system configured to receive the signals and reconstruct therefrom a series of medical images of the subject. In one version of the system, a second series of medical images is concurrently acquired using an x-ray computed tomography imaging device. In one version of the system, a second series of medical images is concurrently acquired using a magnetic resonance imaging device.

Administration to the subject of a pharmaceutical composition including radiolabeled cells for in vivo detection of the accumulated cells in a target region of the subject can be accomplished intravenously, intraarterially, intrathecally, intramuscularly, intradermally, subcutaneously, or intracavitary. A "subject" is a mammal, preferably a human. In the method of the invention, sufficient time is allowed after administration of a detectable amount of the radiolabeled cells such that the radiolabeled cells can accumulate in a target region of the subject. A "detectable amount" means that the amount of the detectable radiolabeled cells that is administered is sufficient to enable detection of accumulation of the radiolabeled cells in a subject by a medical imaging technique.

One non-limiting example method of imaging according to the invention involves the use of an intravenous injectable composition including radiolabeled cells or viruses. A positron emitting atom of the radiolabeled cells or viruses gives off a positron, which subsequently annihilates and gives off coincident gamma radiation. This high energy gamma radiation is detectable outside the body through the use of positron emission tomography imaging, or positron emission tomography concurrent with computed tomography imaging (PET/CT). With PET/CT, the location of the injected and subsequently accumulated labeled cells within the body can be identified.

EXAMPLES

The following Examples are provided in order to demonstrate and further illustrate certain embodiments and aspects of the present invention and are not to be construed as limiting the scope of the invention.

Example 1

Overview of Example 1

Background: With the recent growth of interest in cell-based therapies and radiolabeled cell products, there is a need to develop more robust cell labeling and imaging methods for in vivo tracking of living cells. This study in Example 1 describes evaluation of a novel cell labeling approach with the PET isotope $^{89}$Zr ($T_{1/2}$=78.4 hours). Zr-89 may allow PET imaging measurements for several weeks and take advantage of the high sensitivity of PET imaging.

Methods: A novel cell-labeling agent, $^{89}$Zr-desferrioxamine-NCS ($^{89}$Zr-DBN), was synthesized. Mouse derived melanoma cells (mMCs), dendritic cells (mDCs) and human mesenchymal stem cells (hMSCs) were covalently labeled with $^{89}$Zr-DBN via the reaction between the NCS group on $^{89}$Zr-DBN and primary amine groups present on cell surface membrane protein. The stability of the label on the cell was tested by cell efflux studies for 7 days. The effect of labeling on cellular viability was tested by proliferation, trypan blue and cytotoxicity/apoptosis assays. The stability of label was also studied in in vivo mouse models by serial PET scans and ex vivo biodistribution following intravenous and intramyocardial injection of $^{89}$Zr-labeled hMSCs. For comparison, imaging experiments were performed after intravenous injections of $^{89}$Zr hydrogen phosphate ($^{89}$Zr(HPO$_4$)$_2$).

Results: The labeling agent, $^{89}$Zr-DBN, was prepared in 55±5% decay-corrected radiochemical yield measured by silica gel iTLC. The cell labeling efficiency was 30-50% after 30 minutes labeling depending on cell type. Radioactivity concentrations of labeled cells of up to 0.5 MBq/1×10$^6$ cells were achieved without a negative effect on cellular viability. Cell efflux studies showed high stability of the radiolabel out to 7 days. Myocardially delivered $^{89}$Zr-labeled hMSCs showed retention in the myocardium, as well as redistribution to lung, liver and bone, whereas intravenous delivery of $^{89}$Zr-labeled hMSCs distributed primarily to lung, liver and bone which are expected distribution sites for human MSCs in mouse model. $^{89}$Zr(HPO$_4$)$_2$ distributed to liver and bone with no activity in lung. Thus, the in vivo stability of the radiolabel on the hMSCs was evidenced.

Conclusions: We have developed a robust, general, and biostable $^{89}$Zr-DBN based cell-labeling strategy with promise for wide applications of PET-based non-invasive in vivo cell trafficking.

Methods

Cell Culture

B16-F10 Mouse melanoma cells (mMCs) from ATCC, Manassas, Va., USA, human mesenchymal stem cells (hMSCs) from patients and JAWSII mouse dendritic cells (mDCs) from ATCC, Manassas, Va., USA, were used for evaluating the $^{89}$Zr-DBN based labeling method. The mMCs and hMSCs were cultured in complete DMEM (DMEM+ 10% FBS) and mDCs were cultured in complete alphaMEM (alpha MEM+4 mM L-glutamine+1 mM sodium pyruvate+5 ng/mL murine GM-CSF+20% FBS). The cultures were maintained in a humidified cell culture chamber (21% O$_2$, 74% N$_2$, 5% CO$_2$) at 37° C.

Production and Isolation of $^{89}$Zr $^{89}$Zr$^{4+}$ was produced in aqueous solution through the $^{89}$Y(p,n)$^{89}$Zr nuclear reaction using a solution target containing yttrium nitrate and dilute nitric acid. The $^{89}$Zr$^{4+}$ was isolated from $^{89}$Y$^{3+}$ using a hydroxamate resin based purification method with the exception that the final elution of $^{89}$Zr$^{4+}$ off the hydroxamate resin was performed with an appropriate volume of 1.2M K$_2$HPO$_4$/KH$_2$PO$_4$ buffer (pH 3.5). The K$_2$HPO$_4$/KH$_2$PO$_4$ buffer was allowed to sit on the column for 30 minutes before elution to promote release of $^{89}$Zr as Zirconium hydrogen phosphate, $^{89}$Zr(HPO$_4$)$_2$ from the column. The elution percentage of $^{89}$Zr from the column was ~89% collected in four fractions of 0.5 mL each.

Synthesis of $^{89}$Zr-DBN

The eluted $^{89}$Zr(HPO$_4$)$_2$ solution (120 µl) was neutralized to pH 7.8 with ~100 µl 1M HEPES-KOH buffer (pH 7.5) and ~65 µl 1M K$_2$CO$_3$. To this, 4 µl 5 mM DFO-Bz-NCS in DMSO (Macrocylics, Dallas, Tex., USA) was added and chelation of $^{89}$Zr$^{4+}$ proceeded at 37° C. for 1 hour in a thermomixer at 550 rpm. Chelation efficiency was determined by silica gel iTLC (Agilent Technologies, Santa Clara, Calif., USA) with 50 mM DTPA pH 7 as the mobile phase. $^{89}$Zr-DBN showed an R$_f$=0, whereas $^{89}$Zr(HPO$_4$)$_2$ had an R$_f$=0.9.

Labeling of Cells with $^{89}$Zr(HPO$_4$)$_2$ and $^{89}$Zr-DBN

The adherent cells were trypsinized and washed once with PBS and twice with HEPES buffered GIBCO Hanks Balanced Salt solution buffered (ThermoFisher, Atlanta, Ga., USA) (H-HBSS), pH 7.5. The cell labeling reaction was performed with ~6×10$^6$ cells in 500 µl H-HBSS at pH 7.5. To this, either 100 µl $^{89}$Zr(HPO$_4$)$_2$ (~6 MBq) or 100 µl $^{89}$Zr-DBN (~6 MBq) was added and was allowed to incubate at 37° C. for 30 minutes on a shaker for cell labeling. After incubation, the cells were washed 4 times with appropriate volume of complete medium. The final labeling efficiency was calculated from the radioactivity bound to cells after all the washes.

Incorporation of $^{89}$Zr-DBN in Protein Fraction

To understand the sub-cellular localization of the label, incorporation of $^{89}$Zr-DBN into different protein fractions in mMCs, hMSCs and mDCs was evaluated using a subcellular protein fractionation kit (Piercenet Thermo Scientific) at day 1, 4 and 7 post-labeling. The cytosolic proteins, hydrophobic membrane proteins, nuclear proteins and cytoskeletal proteins were isolated and each protein fraction was counted for radioactivity using a 2480 Wizard$^2$ automatic gamma counter (Perkin Elmer, Waltham, Mass., USA).

Efflux of $^{89}$Zr-DBN from Labeled Cells

To determine cellular efflux, 0.3×10$^6$ $^{89}$Zr-labeled cells were plated into each well of a 6-well culture plate. The medium was replaced with fresh medium daily for 7 days and radioactivity in the replaced medium was counted. For mDCs with mix of adherent and suspension cells, the plate was centrifuged at 1000 rpm for 10 minutes before replacing the medium to avoid loss of unattached $^{89}$Zr-labeled cells.

CyQUANT Cellular Proliferation Assay

The effect of radiolabeling on cellular proliferation was assessed by the CyQUANT DNA content assay (ThermoFisher, Atlanta, Ga., USA). A known number of unlabeled and $^{89}$Zr-labeled cells (~10$^4$ cells/well) were plated in 21 wells of a 96-well culture plate and maintained at 37° C. in a CO$_2$ incubator. The amount of DNA in each well was quantified from absorbance values as a surrogate marker of the number of cells present. The culture medium was replaced daily. The CyQUANT assay was performed for 3 wells per day over 5 days.

Trypan-Blue Exclusion Assay Cellular Viability Test

The effect of labeling on cellular viability was assessed using Trypan-Blue exclusion assay test within 1 hour of labeling, 3$^{rd}$ and 7$^{th}$ day post-labeling. The culture medium was replaced daily and maintained at 37° C. in a CO$_2$ incubator. Unlabeled cells served as control.

ApoTox-Glo Viability/Cytotoxicity and Apoptosis Assay

The effect of radiolabeling on cellular viability was also assessed using the ApoTox-Glo viability, cytotoxicity and caspase 3/7 apoptosis assay (Promega Corporation, Madison, Wis., USA). Unlabeled cells served as control. A known number of unlabeled and $^{89}$Zr-labeled cells (~10$^4$/well) were plated in a 96-well culture plate. The culture medium was replaced daily and maintained at 37° C. in a CO$_2$ incubator. At day 7, cell viability, cytotoxicity and apoptosis was quantified in triplicate using the ApoTox-Glo assay. As positive controls, cells were incubated with 30 µg/mL digitonin for 30 minutes for the viability and cytotoxicity assays, while 2 µM staurosporine was added for 16 hours for the caspase 3/7 dependent apoptosis assay.

PET Imaging and Ex-Vivo Biodistribution of $^{89}$Zr-Labeled Cells and $^{89}$Zr(HPO$_4$)$_2$ Experiments were performed with 2-month old athymic nude Foxn1nu mice (Harlan Laboratories, Inc., Indianapolis, Ind., USA). $^{89}$Zr(HPO$_4$)$_2$ (~0.074 MBq) or $^{89}$Zr-labeled cells (2×10$^5$ cells with radioactivity concentration ~0.37 MBq/1×10$^6$ cells) were injected intravenously through a tail vein. On days 2, 4, and 7, the mice were anesthetized under 1-2% isoflurane and underwent PET imaging using a small animal PET/X-Ray system (Sofie BioSystems Genesys4, Culver City, Calif., USA). At day 7, the mice were sacrificed and tissues were extracted and radioactivity counted using a gamma counter to evaluate the biodistribution of $^{89}$Zr-radioactivity. Images were presented as a whole-body maximal images projection (MIPs) to display sites of uptake.

In Vivo Tracking of Stem Cell Engraftment in Ischemia/Reperfusion Mouse Model

Athymic nude Foxn1nu mice (2 months old) were anesthetized under 1-2% isoflurane and placed on a heating pad. Respiratory and heart rates were monitoring continually. After intubation, mechanical ventilation and intercostal block of bupivacaine and lidocaine, an incision was made in through the $4^{th}$ or $5^{th}$ intercostal space for access into the thoracic space, the heart was exposed and the pericardium was incised anterior and parallel to the phrenic nerve. With visualization of the coronary vasculature, the left coronary artery was ligated to induce myocardial ischemic at the anterior wall of the left ventricle. One hour after the coronary ligation, the suture was untied for reperfusion. Myocardial reperfusion was confirmed by color change of the left ventricle and electrocardiographic changes. During reperfusion, $^{89}$Zr-labeled cells ($2\times10^5$ cells with radioactivity concentration ~0.37 MBq/$10^6$ cells) were injected at 4 sites within the ischemic region. After myocardial injection, the intercostal space, the chest musculature and the skin were closed with a 7-0 Ethilon suture. The animals were imaged at day 2, day 5 and day 7 using small animal PET/X-Ray system (Sofie BioSystems Genesys4, Culver City, Calif., USA). At day 7, the mice were sacrificed and tissues were extracted and radioactivity counted using gamma counter to evaluate cell trafficking.

Results

Synthesis of $^{89}$Zr-DBN and Cell Labeling Studies $^{89}$Zr hydrogen phosphate was readily chelated by DFO-NCS to form $^{89}$Zr-DBN in a 1.2 M $K_2HPO_4/KH_2PO_4$ and HEPES buffer system (pH 7.8), with radiolabeling efficiency of 55±5% after 30 minutes. This reaction mixture was then used directly for labeling of cells. The cell labeling efficiency using $^{89}$Zr-DBN was ~30-50% as determined by cell-bound radioactivity. Radioactivity concentrations of 0.50±0.10, 0.47±0.10, and 0.39±0.20 MBq/$10^6$ cells were achieved when $6\times10^6$ cells were incubated for 30 minutes with ~6 MBq $^{89}$Zr-DBN with mMCs, hMSCs and mDCs, respectively. In contrast, no cell labeling was observed using $^{89}$Zr(HPO$_4$)$_2$.

Cellular Proliferation and Viability Studies

Figure 3:
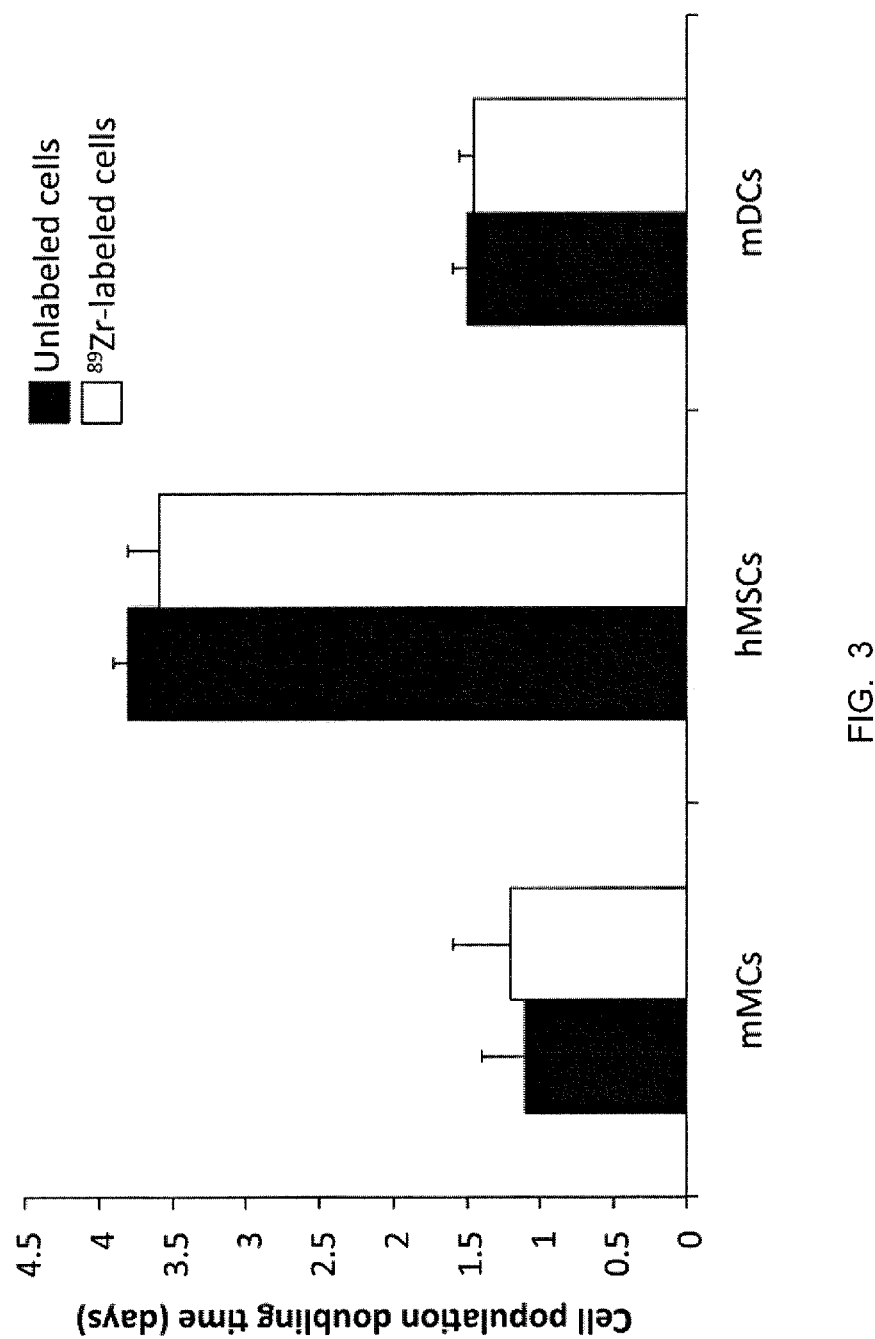
FIG. 3 is a comparison of cell population doubling times for $^{89}Zr$-labeled and unlabeled mMCs, hMSCs and mDCs.

The CyQUANT proliferation assay showed no difference in proliferation rate between unlabeled and $^{89}$Zr-labeled cells. See FIG. 3 for a comparison of cell population doubling times for $^{89}$Zr-labeled and unlabeled mMCs, hMSCs and mDCs. The cells were plated at appropriate cell number at day 3 and CyQUANT assay was performed at day 7 post-labeling. No significant differences were observed between radiolabeled and unlabeled cells. Values in FIG. 3 are shown as mean±standard deviation, n=3.

Trypan Blue cell viability tests were performed on radiolabeled cells immediately after labeling and up to 7 days post-labeling and compared with unlabeled cells. No change was observed in number of dead cells (blue stained cells) over live cells (unstained cells) in both $^{89}$Zr-labeled and unlabeled cells, with percentage of dead cells <5% in all days tested.

ApoTox-Glo Viability/Cytotoxicity and Apoptosis Assay

Figure 4A:
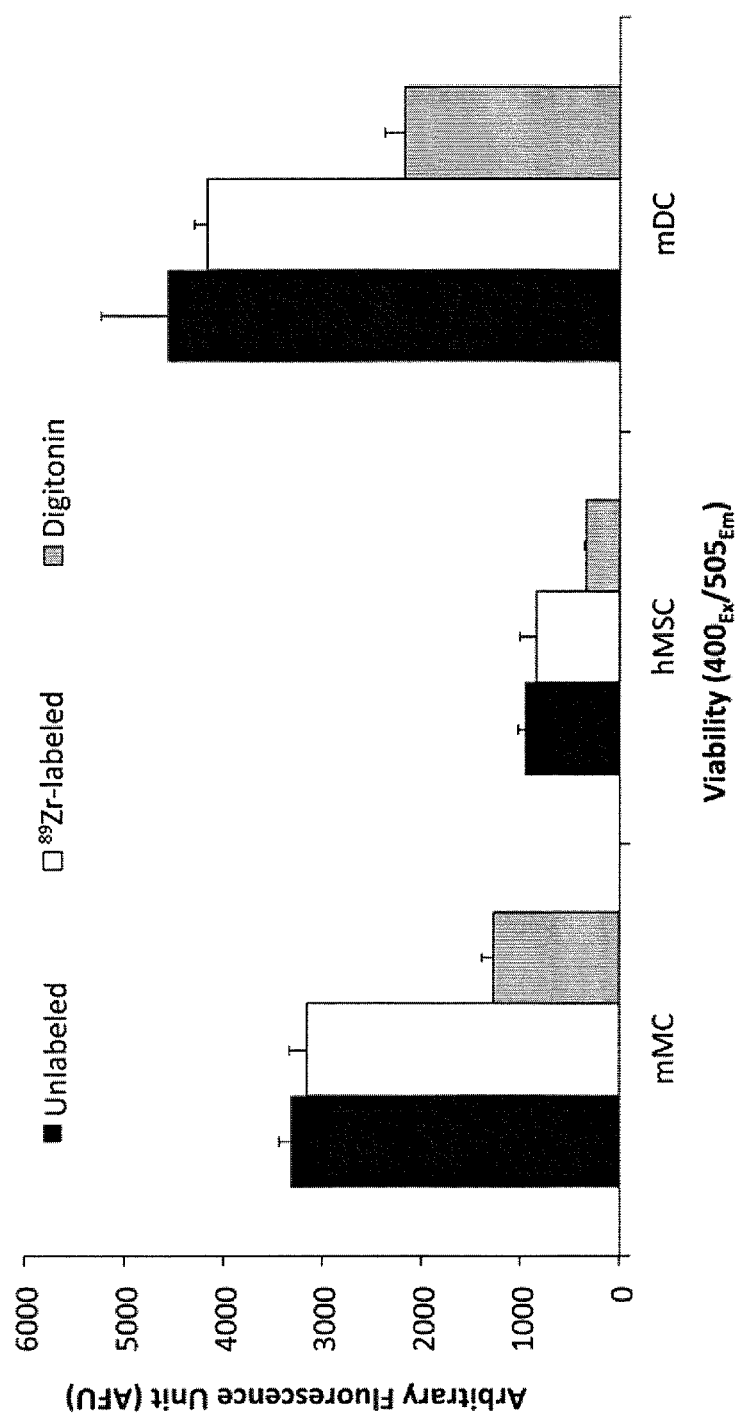
FIG. 4A is a graphical representation of the viability of $^{89}Zr$-labeled and unlabeled cells.
Figure 4B:
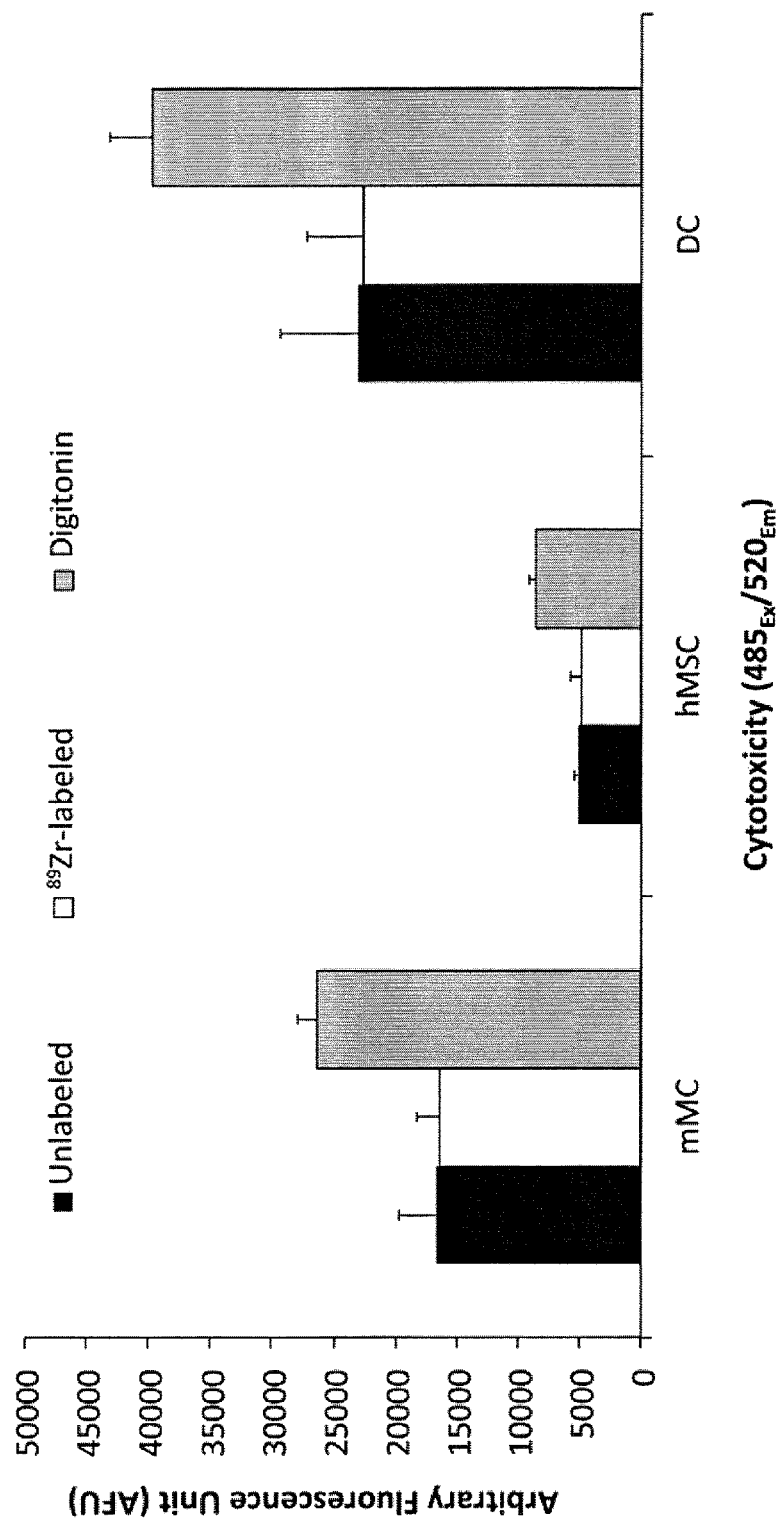
FIG. 4B is a graphical representation of the cytotoxicity of $^{89}Zr$-labeled and unlabeled cells.
Figure 4C:
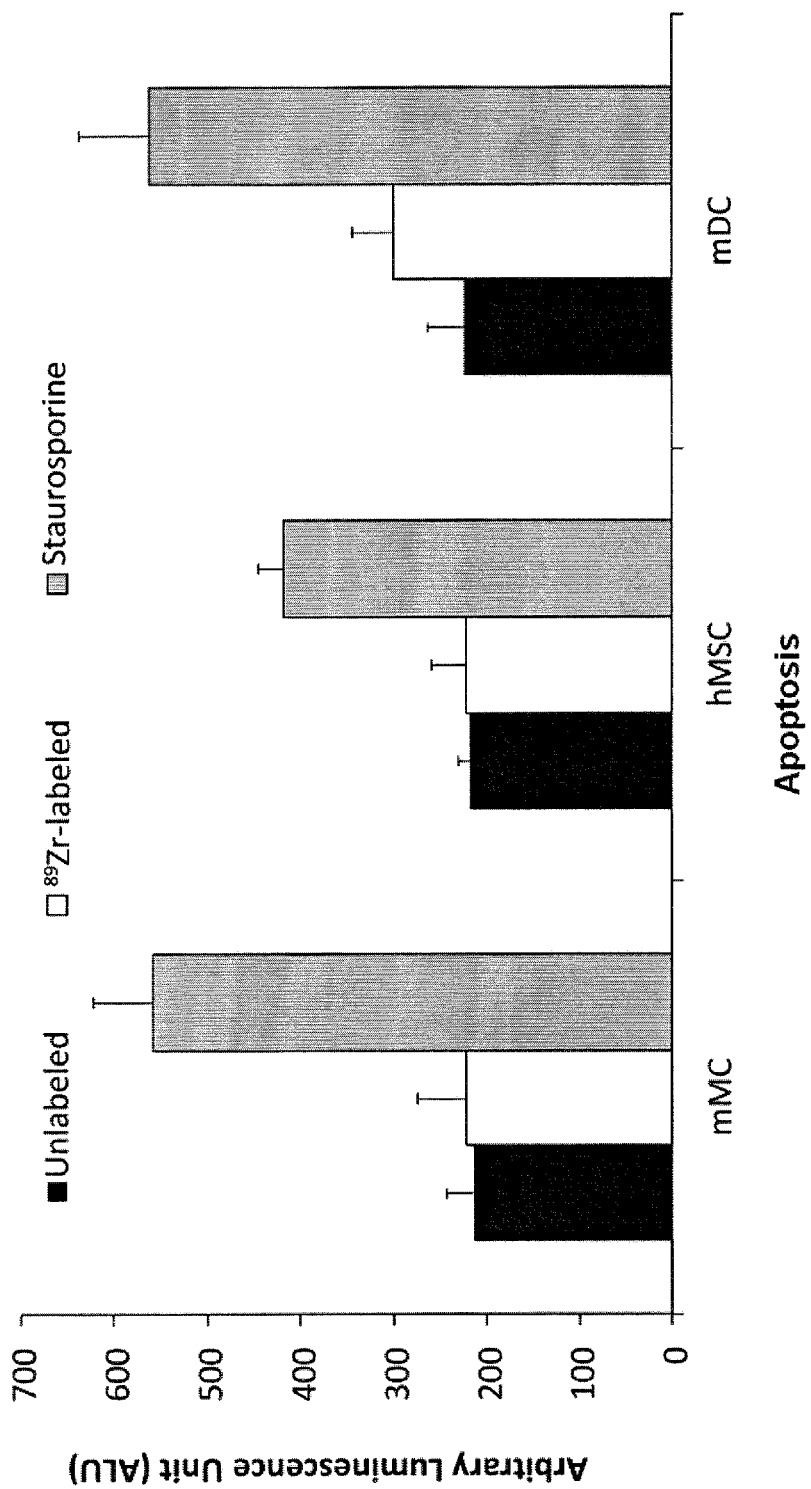
FIG. 4C is a graphical representation of the apoptosis of $^{89}Zr$-labeled and unlabeled cells.

The ApoTox-Glo assay showed no loss in cellular viability and no increase in cytotoxicity or apoptosis in radiolabeled cells as illustrated in FIGS. 4A-4C showing an assessment of (FIG. 4A) viability, (FIG. 4B) cytotoxicity and (FIG. 4C) apoptosis in $^{89}$Zr-labeled and unlabeled cells. No statistically significant differences were observed between $^{89}$Zr-labeled and unlabeled cells after 7 days of culture with regard to viability, cytotoxicity or apoptosis. As positive controls, 30 mg/mL digitonin was used for assays (FIG. 4A) and (FIG. 4B), and 2 mM staurosporine for (FIG. 4C). *p<0.05 versus assessments in $^{89}$Zr-labeled and unlabeled cells using unpaired t-test. Values are shown as mean±standard deviation, n=3. Viability was lost and cytotoxicity enhanced when 30 µg/mL digitonin was added to cells and apoptosis was increased with the addition of 2 µM staurosporine.

Subcellular Distribution of $^{89}$Zr-Radioactivity

At days 1, 4 and 7 after $^{89}$Zr-labeling of mMCs, hMSCs and mDCs, subcellular protein fractionation of the cells was performed. $^{89}$Zr-radioactivity was incorporated predominantly (~99%) in hydrophobic membrane protein fraction of all cell types studied, strongly supporting the proposed mechanism of reaction of $^{89}$Zr-DBN with cell surface membrane protein to form a stable covalent bond.

Efflux of $^{89}$Zr-Radioactivity from Labeled Cells

Figure 5:
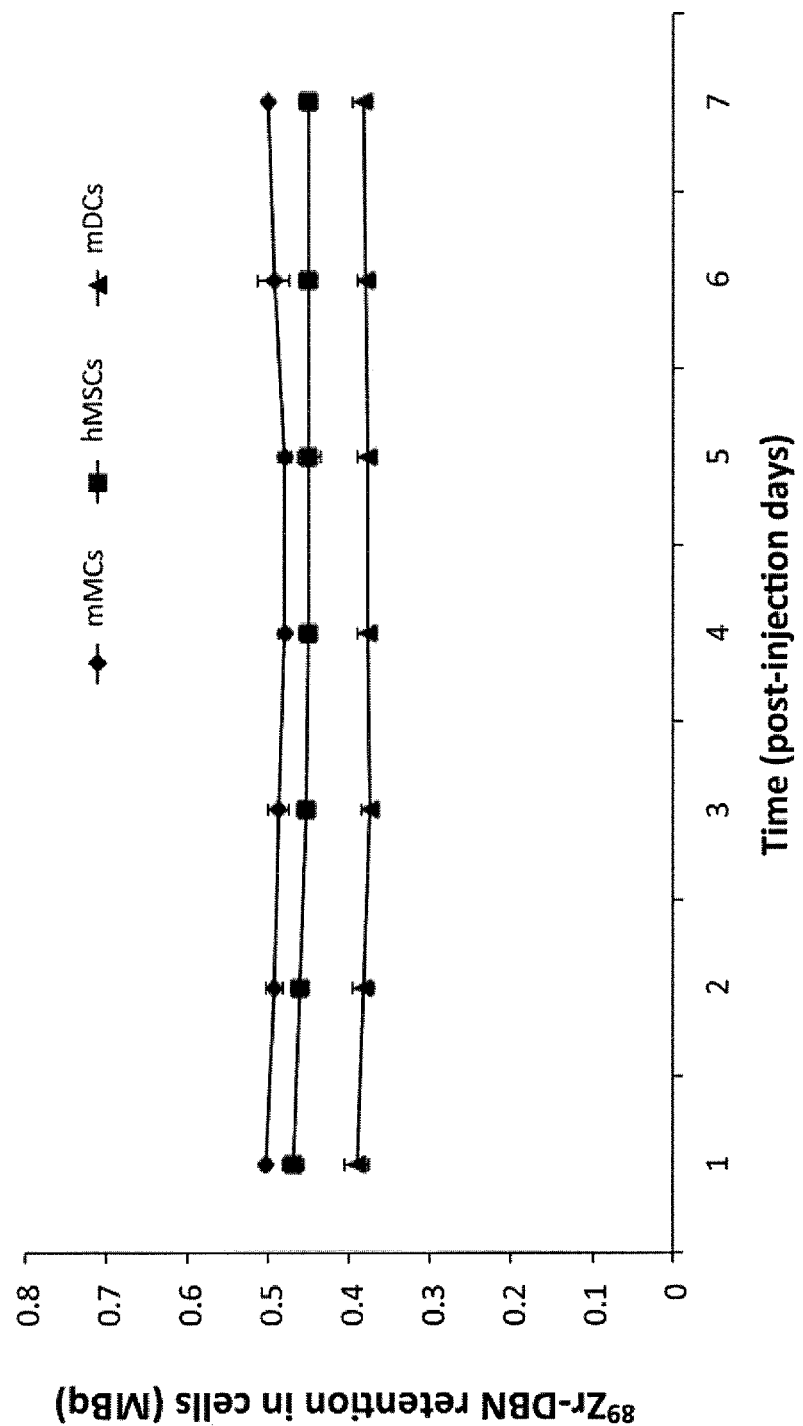
FIG. 5 shows the retention of $^{89}Zr$ in $^{89}Zr$-labeled cells expressed as radioactivity in MBq in the cell population.

Retention of $^{89}$Zr-radioactivity by $^{89}$Zr-DBN labeled cells was found to be stable in all the cells studied with negligible efflux observed over 7 days post-labeling. See FIG. 5 showing retention of $^{89}$Zr in $^{89}$Zr-labeled cells expressed as radioactivity in MBq in the cell population. The retention value is representing total radioactivity/$10^6$ cells in the proliferating cell population. No significant change was observed in retention of $^{89}$Zr in radiolabeled cells. Values are shown as mean±standard deviation, n=3.

PET Imaging and Biodistribution Studies in Mice with Intravenous Injections

Figure 6A:
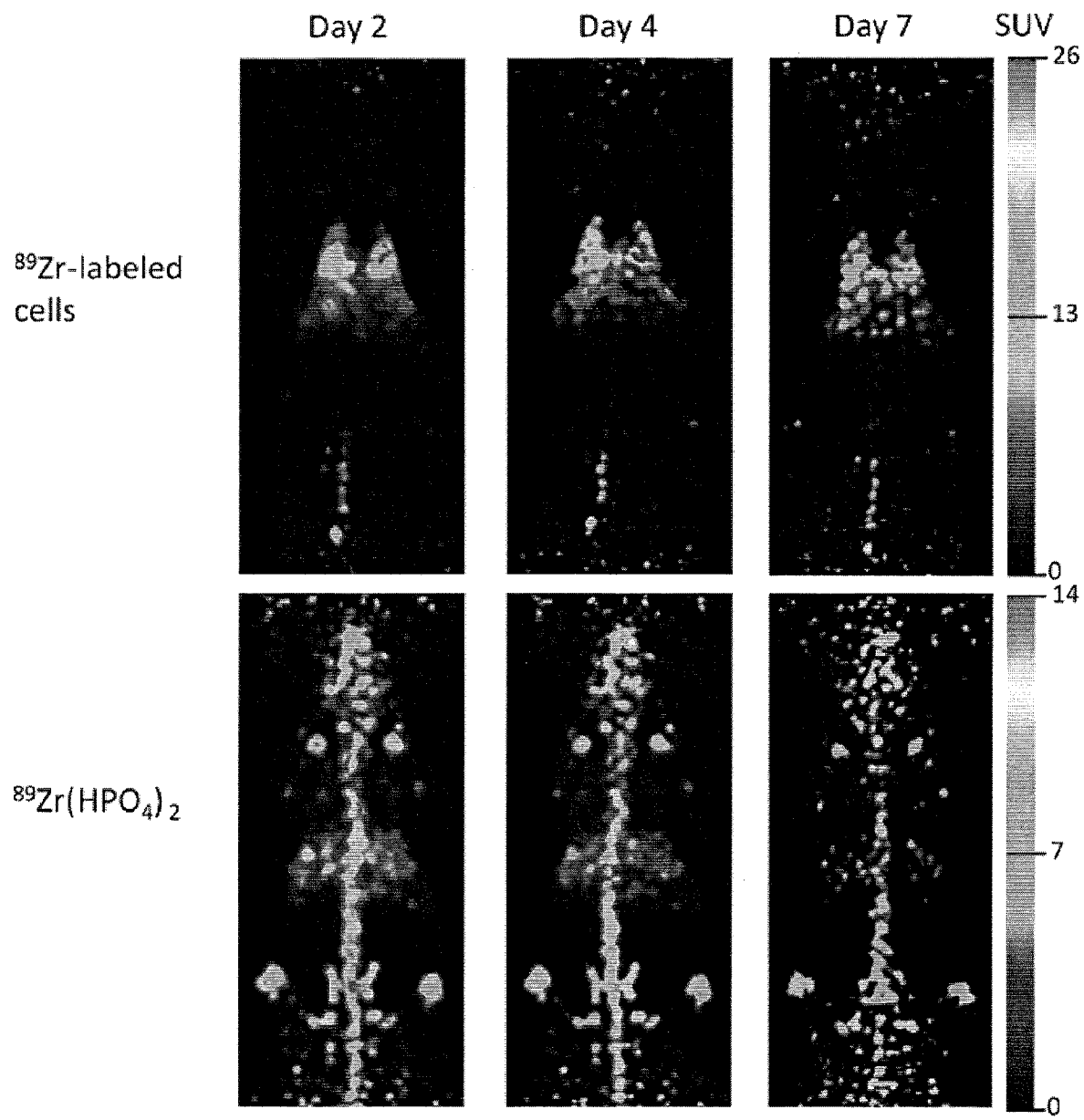
FIG. 6A is representative PET images labeled hMSCs and $^{89}Zr(HPO_4)_2$ following intravenous injection.
Figure 6B:
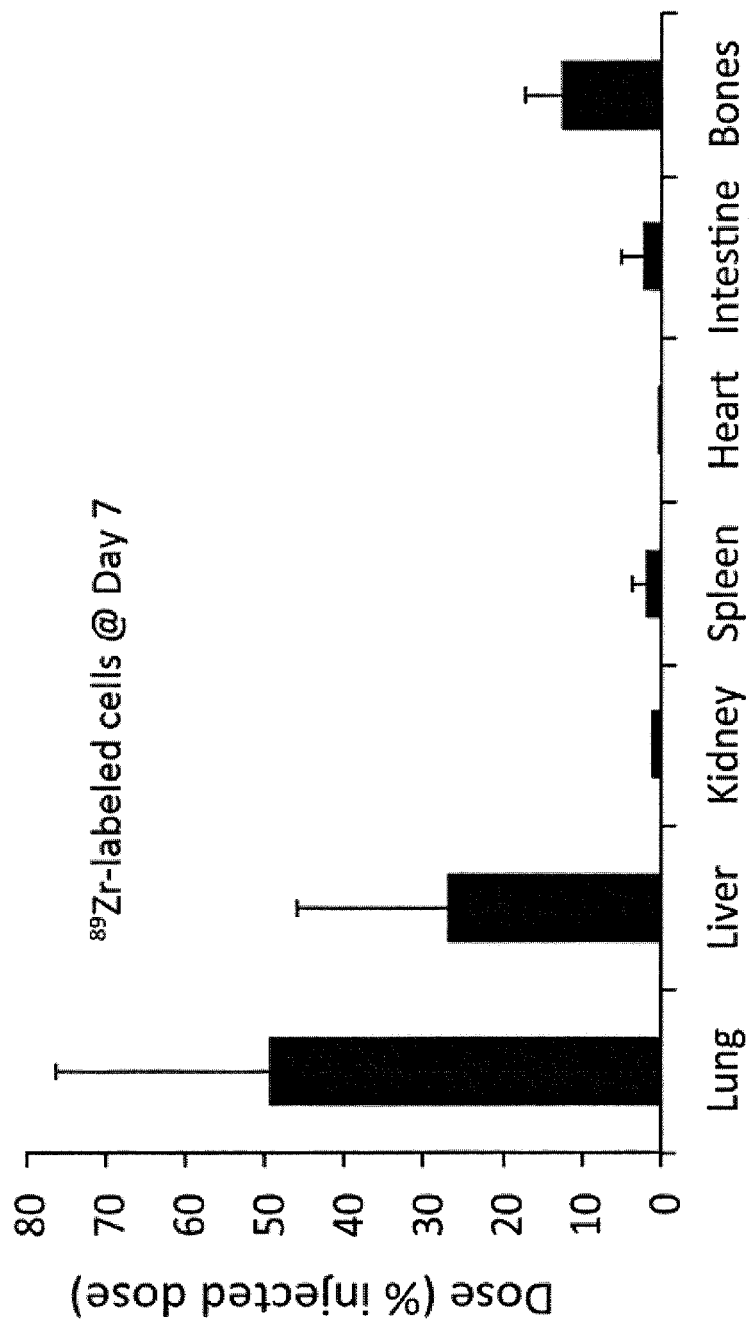
FIG. 6B is biodistribution data of $^{89}Zr$-labeled hMSCs and $^{89}Zr(HPO_4)_2$ following intravenous injection.
Figure 6C:
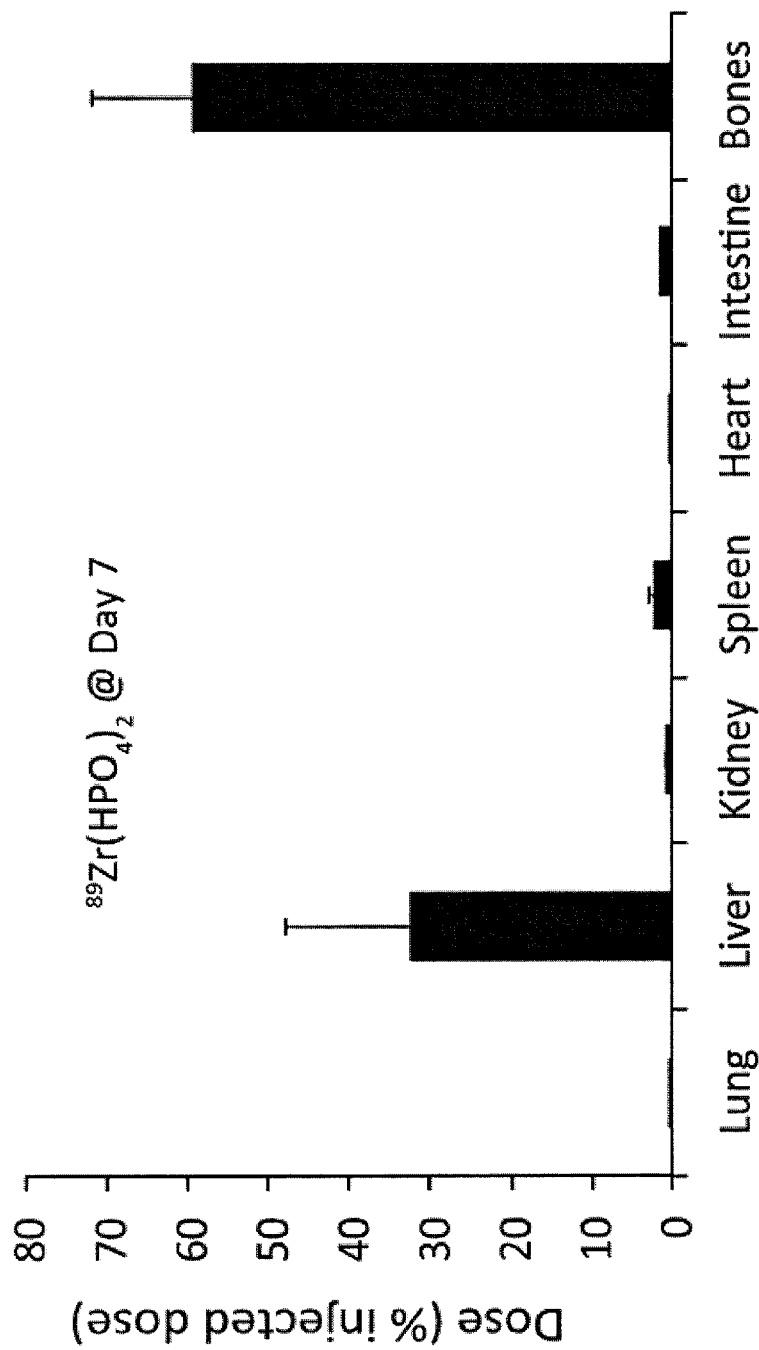
FIG. 6C is biodistribution data of $^{89}Zr(HPO_4)_2$ labeled hMSCs and 89Zr(HPO$_4$)$_2$ following intravenous injection.

PET images and biodistribution data of intravenously administered $^{89}$Zr-labeled hMSCs and $^{89}$Zr(HPO$_4$)$_2$ in healthy mice are in FIGS. 6A-6C which show representative PET images and biodistribution data of $^{89}$Zr-labeled hMSCs and $^{89}$Zr(HPO$_4$)$_2$ following intravenous injection. $^{89}$Zr-labeled human MSCs ($2\times10^5$ cells with radioactivity concentration ~0.37 Mbq/$10^6$ cells) and $^{89}$Zr(HPO$_4$)$_2$ (0.074 Mbq radioactivity) were intravenously injected in athymic mice. Most of the radioactivity was distributed in lung, liver and bones following injection of $^{89}$Zr-labeled hMSCs whereas most of the radioactivity was distributed in liver and bones following injection of $^{89}$Zr(HPO$_4$)$_2$. Values in graphs are shown as mean±standard deviation, n=3. The $^{89}$Zr-labeled hMSCs were concentrated primarily in lung and liver, followed by bone. On the other hand, $^{89}$Zr(HPO$_4$)$_2$ accumulated in bone and liver and did not distribute to lung.

In Vivo Tracking of Stem Cell Engraftment in Ischemia/Reperfusion Mouse Model

Figure 7A:
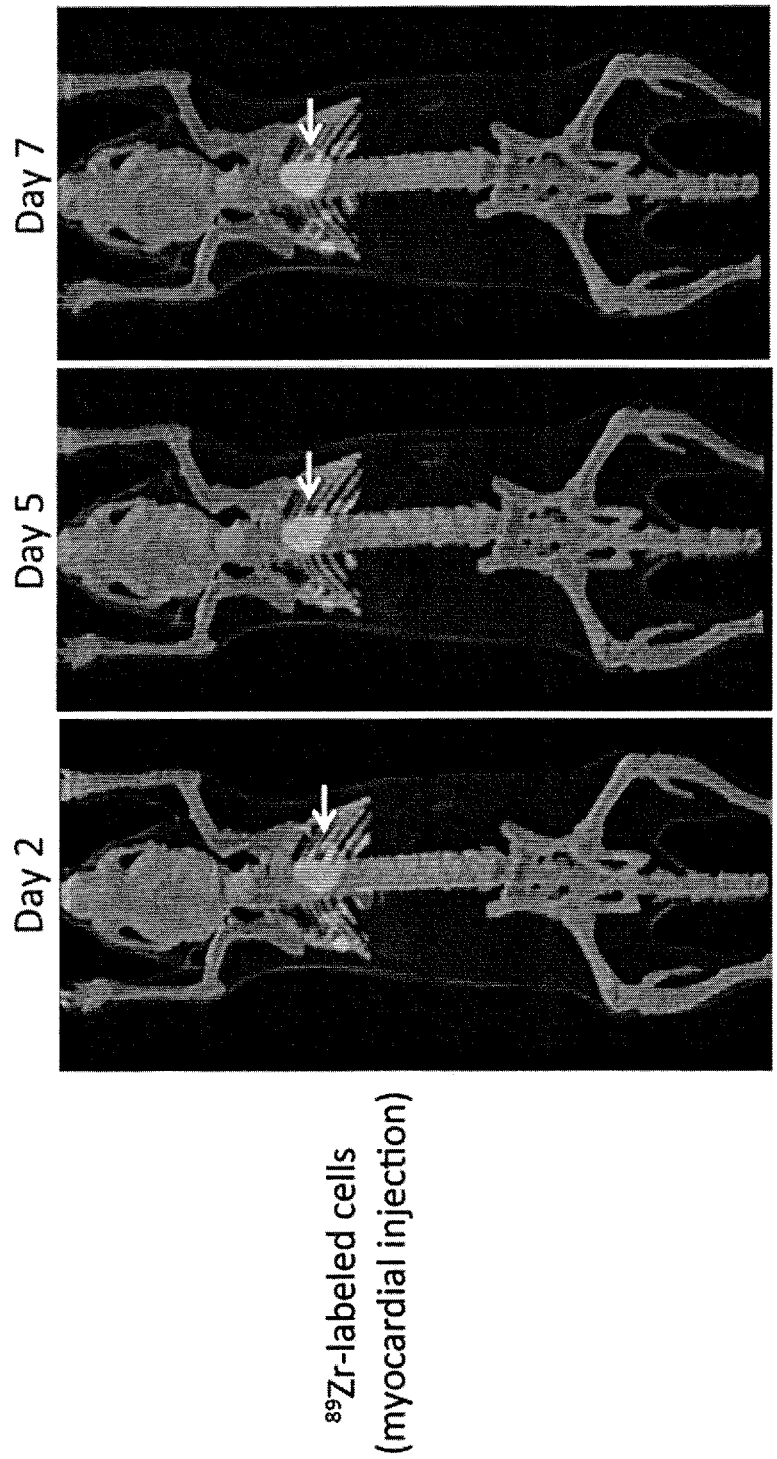
FIG. 7A shows representative PET images of $^{89}$Zr-labeled hMSCs following myocardial delivery.
Figure 7B:
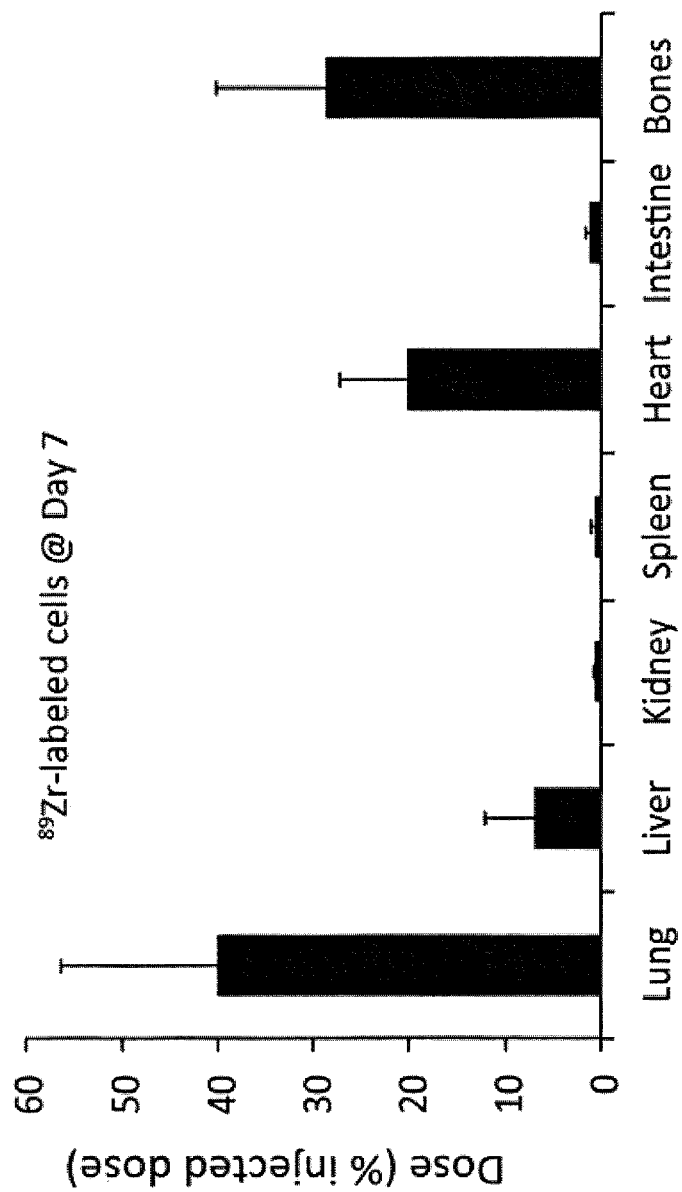
FIG. 7B is representative biodistribution data of $^{89}$Zr-labeled hMSCs following myocardial delivery.

Following myocardial delivery, $^{89}$Zr-labeled hMSCs (~19.5±9.5%) were retained for 7 days in heart. See FIGS. 7A-7B for representative PET images and biodistribution data of $^{89}$Zr-labeled hMSCs following myocardial delivery. $^{89}$Zr-labeled hMSCs ($2\times10^5$ cells with radioactivity concentration ~0.37 Mbq/$10^6$ cells) were delivered to myocardium of an ischemia/reperfusion mouse model. Most of the radioactivity was distributed in heart (arrow), lung, liver and bones following myocardial delivery of $^{89}$Zr-labeled hMSCs. Values in graph are shown as mean±standard deviation, n=5. The remaining cells were concentrated in lung, followed by bones and liver. The higher uptake in lung relative to liver is consistent with the biodistribution of $^{89}$Zr-labeled hMSCs released into the circulation (FIGS. 6A-6C).

Discussion

Various strategies have been employed in the past to label cells with imaging isotopes for non-invasive in vivo cell tracking for cell based therapies and infection imaging. Among them, $^{18}$F-FDG (for PET) [Ref. 12-16] and $^{111}$In-oxine (for SPECT) [Ref. 2-6] are the most widely used. Although $^{18}$F-FDG is useful for assessment of immediate delivery of cells and early fate of cells (first few hours), it is not suited for in vivo cell tracking after 24 hours post-injection due to its short half-life and poor retention in cells. Inability of $^{18}$F-FDG to allow cell tracking after 24 hours limits its utility in cell-based therapies. For cell-based therapies, early engraftment period of 2-5 weeks post cell delivery is the most critical time period [Ref. 20]. Therefore, imaging based methods should be robust over this time frame to allow evaluation of various interventions for improving cell engraftment. The ability to monitor cells in vivo beyond 24 hours is also of high importance for evaluation of infection using radiolabeled leukocytes. Conventional infection imaging protocols perform imaging at 1 hours, 4 hours and 24 hours post-injection to differentiate between inflammatory, acute infection and chronic infection loci, however in some patients, 48 hours was necessary for reliable detection of infected lesions [Ref. 21].

The use of $^{111}$In ($T_{1/2}$=2.8 days) as a radiolabel for cell labeling allows longer observation periods for cell tracking but with lower spatial resolution of SPECT imaging. Cell labeling with $^{111}$In typically requires a lipophilic carrier molecule (e.g. oxine) for transporting the radiometal into cells [Ref. 2-6]. After entering the cells, the radiometal then dissociates and gets trapped in the cell by binding to non-specific intracellular metal-binding proteins. The two major disadvantages of this approach are chemotoxicity of the lipophilic carrier molecule [Ref. 22] and efflux of radiolabel from cells [Ref. 2-6].

Recently, two groups (Charoenphun et al. [Ref. 9] and Davidson-Moncada et al. [Ref. 10]) reported synthesis of $^{89}$Zr-oxinate or $^{89}$Zr-oxine as a cell-labeling reagent for PET based cell tracking. As expected, both groups faced the problem of chemotoxicity and significant efflux of radioactivity from the cells post-labeling commonly associated with oxine based labeling. Charoenphun et al. [Ref. 9] showed reduced viability of $^{89}$Zr-oxine labeled 5T33 myeloma cells (from 93% to 76.3±3.2% in first 24 hours) and significant efflux of radioactivity post-labeling (29% effluxed in 24 hours). Davidson-Moncada et al. [Ref. 10] also reported similar results with $^{89}$Zr-oxine labeled human and rhesus macaques' natural killer cells. They observed a broad range of viability of 60-100% in the radiolabeled cells over the first 24 hours, which declined to 20-30% after 6 days. A significant efflux of radioactivity was also observed in these viable $^{89}$Zr-oxine labeled cells, ~20-25% effluxed in the first 24 hours and 70-80% of radioactivity was effluxed after 7 days of culture. These drawbacks associated with the $^{89}$Zr-oxine labeling method compromises its utility for PET-based monitoring of in vivo cell trafficking.

To improve the stability of the $^{89}$Zr radiolabel on cells, this Example proposed $^{89}$Zr-DFO-NCS ($^{89}$Zr-DBN) as a labeling entity capable of forming covalent bonds with primary amines of cell surface protein (see FIG. 1). Since all cells express cell surface protein with exposed lysine residues and other primary amines, this strategy also provides a general labeling method to label a broad array of cells. The new strategy exploits both the strength of chelation of $^{89}$Zr by DFO with three hydroxamate groups (qualitative Zr-binding constant=~$10^{31}$) [Ref. 23-26] as well as the inherent biostability of the thiourea bond that conjugates—NCS group in $^{89}$Zr-DBN to primary amines of protein [Ref. 27,28]. Furthermore, the labeling agent, $^{89}$Zr-DBN, is also expected to be well-tolerated by cells as opposed to toxic lipophilic carrier molecules like oxine, relying on the fact that DFO-NCS has been routinely used to conjugate DFO to IgG and IgM antibodies with no loss of antibody protein function [Ref. 23, 26-29]. The generality of the labeling target, along with the multiplicity of primary amines available on the cell surface, also avoids the specific targeting of highly sensitive processes that might affect cellular function or viability. In this study, 30-50% labeling efficiencies were achieved with $^{89}$Zr-DBN in several cell types and the cells showed no evidence of chemotoxicity or radiotoxicity. Furthermore, in contrast with the previously noted $^{89}$Zr-oxine results [Ref. 9,10], no efflux of radiolabel was observed from cultured cells labeled with $^{89}$Zr-DBN out to 7 days. All $^{89}$Zr-radioactivity was found to be incorporated into the membrane bound protein fraction of the cells confirming the anticipated targeting of membrane protein.

After encouraging in vitro validation tests, in vivo validations were performed by investigating the biodistribution of $^{89}$Zr-labeled hMSCs after intravenous injection in athymic nude mice for 7 days post-injection. Trapping of MSCs in lungs following intravenous injection is well documented [Ref. 30,31]. Therefore, major accumulation of $^{89}$Zr-labeled human MSCs in mouse lungs was expected following intravenous injection with slow clearance. With time, cells were expected to dislodge from this physical pulmonary entrapment and distribute to other organs. As expected, the majority of intravenously injected $^{89}$Zr-labeled hMSCs were trapped in lung (50±27%) and the remainder was found in liver (27±19%) and bones (16±5%) after 7 days post-injection, which are expected homing sites for injected mesenchymal stem cells after dislodging from lung [Ref. 32,33]. This was in contrast to the biodistribution of $^{89}$Zr (HPO$_4$)$_2$, which distributed primarily in bone (59±13%) and liver (32±15%) but did not accumulate in lungs. The distinct biodistributions of $^{89}$Zr-labeled hMSCs and $^{89}$Zr(HPO$_4$)$_2$, together with the stability of radiolabel and lack of cytotoxicity strongly supports the robustness of the $^{89}$Zr-DBN based cell labeling approach.

To further test the application of $^{89}$Zr-labeled hMSCs, a stem cell engraftment study was performed using a myocardial acute ischemia/reperfusion mouse model. $^{89}$Zr-labeled hMSCs were delivered to the myocardium of athymic mice following an acute myocardial ischemia/reperfusion insult. After 7 days post-delivery, $^{89}$Zr-labeled hMSCs were found in heart (20±7%), lung (40±16%), bone (29±11%) and liver (7±5%). The observed retention in heart is in accordance with previously published work on hMSC engraftment estimated by invasive quantitative PCR method in a similar rodent model [Ref. 34].

Low levels of in vitro demetalation of $^{89}$Zr-DFO complexes (2-3%/wk) in serum at 37° C. have been reported [Ref. 23, 29] and clinical studies using $^{89}$Zr-DFO labeled antibodies out to 7 days have yet to show significant bone uptake of $^{89}$Zr indicative of demetalation [Ref. 35-39]. The initial Example 1 findings of distribution of $^{89}$Zr-labeled hMSCs in mouse models confirm the biostability of the radiolabel bound to the DFO moiety supporting further exploration of the $^{89}$Zr-DBN labeling method for monitoring stem cell engraftment and cell trafficking.

Conclusions

The $^{89}$Zr-DBN labeling agent is shown to be a robust, general, and biostable cell labeling strategy for. PET-based non-invasive in vivo cell or virus tracking.

Example 2

In this Example, we report the synthesis and evaluation a novel virus labeling agent, $^{89}$Zr-desferrioxamine-NCS ($^{89}$Zr-DBN) for non-invasive PET based in vivo tracking of administered virus.

Background

There is a growing interest in using viral based gene therapy for treating wide range of diseases. Viral based gene delivery agents for gene therapy hold tremendous promise but like drugs, a better understanding of their pharmacokinetics is critical to their advancement. This Example 2 study describes a novel viral labeling approach with $^{89}$Zr ($T_{1/2}$=78.4 h) for potential PET imaging of viral biodistribution in the body.

Methods

A new viral labeling agent, $^{89}$Zr-desferrioxamine-NCS ($^{89}$Zr-DBN), was synthesized. The adeno-associated viruses (AAVs) were covalently labeled with $^{89}$Zr-DBN via the reaction between the NCS group on $^{89}$Zr-DBN and primary amine groups present on capsid/envelope protein. The viral radiolabeling yield was quantified, following which cell binding and cell-infection assays were performed using 293T cells to evaluate the transfection potential of purified $^{89}$Zr-DBN-AAV2-GFP. In addition to this, in vivo biodistribution of intravenous delivered $^{89}$Zr-DBN-AAV1-Cre was assessed by PET imaging and correlated with transfection profile by bio-luminescence imaging (Lum) in a mouse model system.

Results

The scAAV1-Cre and AAV2-GFP were labeled with $^{89}$Zr-DBN with viral labeling yield of ~20 mCi/10$^{14}$ viral particles after 30 minutes of labeling. A cell-binding assay was performed at 4° C. with multiplicity of infection (MOI)=10,000. Following 2 hours of co-incubation of 2.5×10$^9$ $^{89}$Zr-AAV2-GFP particles and 2.5×10$^5$ 293 T cells at 4° C., 7% of the $^{89}$Zr-AAV2-GFP were found to be bound to 293T cells as compared to 0.6% in control group including cells and $^{89}$Zr-hydrogen phosphate ($^{89}$Zr(HPO$_4$)$_2$). In the cell infection assay, $^{89}$Zr-AAV2-GFP was incubated with 293T cells at 37° C. for 5 days, at MOI=2500 and 10,000. The fraction of 293T cells expressing GFP correlated with MOI of $^{89}$Zr-AAV2-GFP. The biodistribution of intravenously injected $^{89}$Zr-AAV1-Cre assessed by PET imaging correlated with the tissue transfection profile assessed by bi-luminescence imaging and fluorescence microscopy.

Conclusions

AAVs were successfully labeled with $^{89}$Zr-DBN. The Zr labeling of AAVs did not affect their viral properties like infection potential and tissue tropism. In principle, $^{89}$Zr-DBN is a promising tool for labeling a wide variety of viruses. Some advantages of this labeling method are that the viral labeling conditions are mild and there is no need for modification of the virus before labeling.

Methods $^{89}$Zr$^{4+}$ was produced in aqueous solution through the $^{89}$Y(p,n)$^{89}$Zr nuclear reaction using a solution target containing yttrium nitrate and dilute nitric acid. The $^{89}$Zr$^{4+}$ was isolated from $^{89}$Y$^{3+}$ using a hydroxamate resin-based purification method in the form of $^{89}$Zr(HPO$_4$)$_2$.

$^{89}$Zr-DBN was synthesized and scAAV1-Cre produced at the Mayo Clinic and AAV2-GFP was purchased from Cell Biolabs, Inc. The scAAV1-Cre and the AAV2-GFP were labeled with $^{89}$Zr-DBN.

Post-labeling, the $^{89}$Zr-DBN-AAVs were purified from free label and reaction mixture using size exclusion PD-10 desalting columns. The eluted virus in fractions were quantified using protein assay and radioactivity elution pattern was recorded.

Purified fractions were tested for infection potential using 293T (for AAV2-GFP) and biodistribution or transfection profile was assessed in in vivo mouse model (for AAV1-Cre) strain FVB.129S6(136)-Gt(ROSA)26Sortm1(Luc)Kael/J from the Jackson Laboratory by PET using Genesys4 PET imaging system (Perkin Elmer) and bioluminescence imaging using Xenogen spectrum imaging system (Perkin Elmer). This mouse strain has ubiquitous expression of red fluorescent protein (RFP) which after transfection with AAV1-Cre changes to green fluorescent protein (GFP) expression. This enabled confirmation of transfection at cellular level using a fluorescence microscope.

Figure 8:
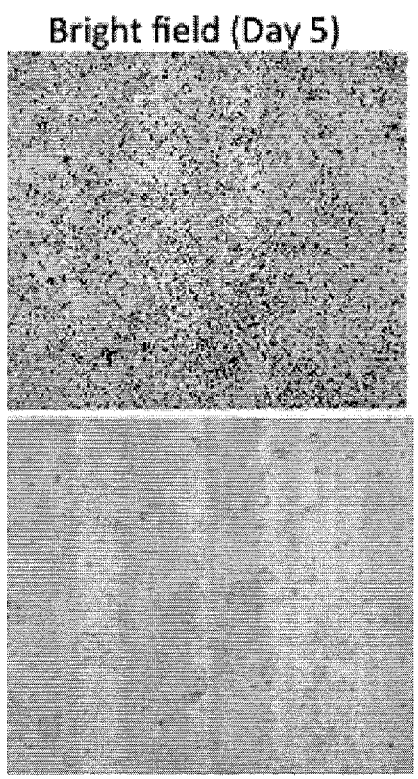
FIG. 8 shows a cell infection assay using $^{89}$Zr-labeled AAV2-GFP and 293T cells.
Figure 8:

FIG. 8 shows representative data showing cell infection assay. Cell infection assay was performed with 2.5×10$^5$ 293 T cells with radiolabeled viral particles (~20 mCi/10$^{14}$ viral particles) at two multiplicity of infection (MOI) ~2500 and 10,000 in DMEM culture medium+1% FBS in CO$_2$ incubator. The GFP signal after 5 day incubation correlated with MOI.

Figure 9:
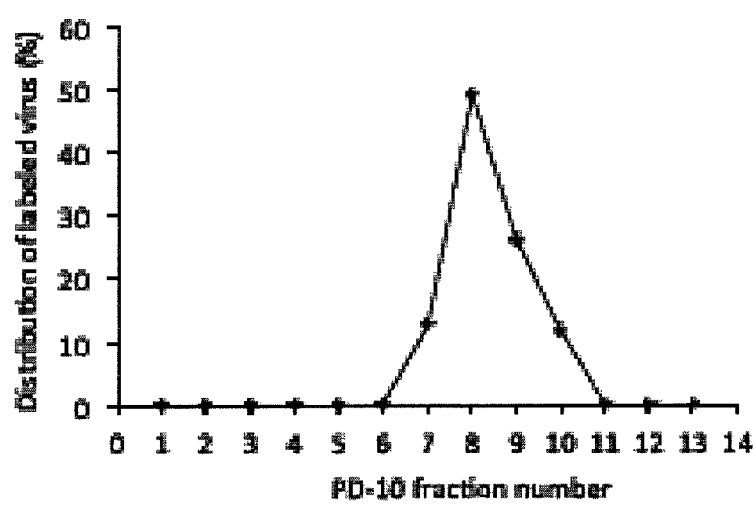
FIG. 9 shows a representative elution profile of labeled AAVs after size exclusion PD-10 column purification.

FIG. 9 shows a representative elution profile of labeled AAVs after size exclusion PD-10 column purification.

Figure 10:
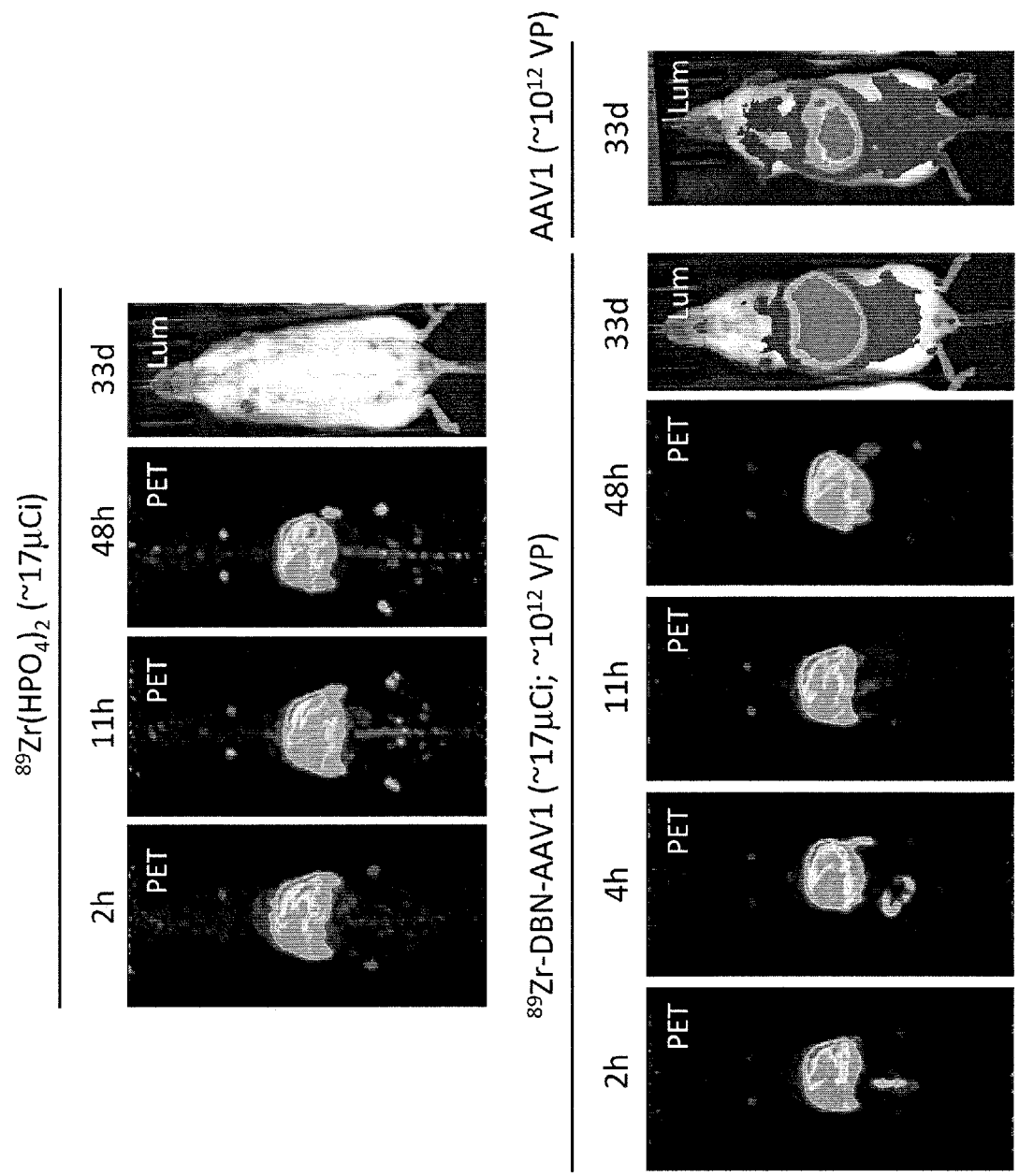
FIG. 10 shows representative serial PET images and bioluminescence images showing biodistribution and transfection profile of $^{89}$Zr-DBN-AAV1-Cre with $^{89}$Zr(HPO$_4$)$_2$ and AAV1 as control.

FIG. 10 shows representative serial PET images and bioluminescence images showing biodistribution and transfection profile of $^{89}$Zr-DBN-AAV1-Cre with $^{89}$Zr(HPO$_4$)$_2$ and AAV1 as control.

Figure 11:
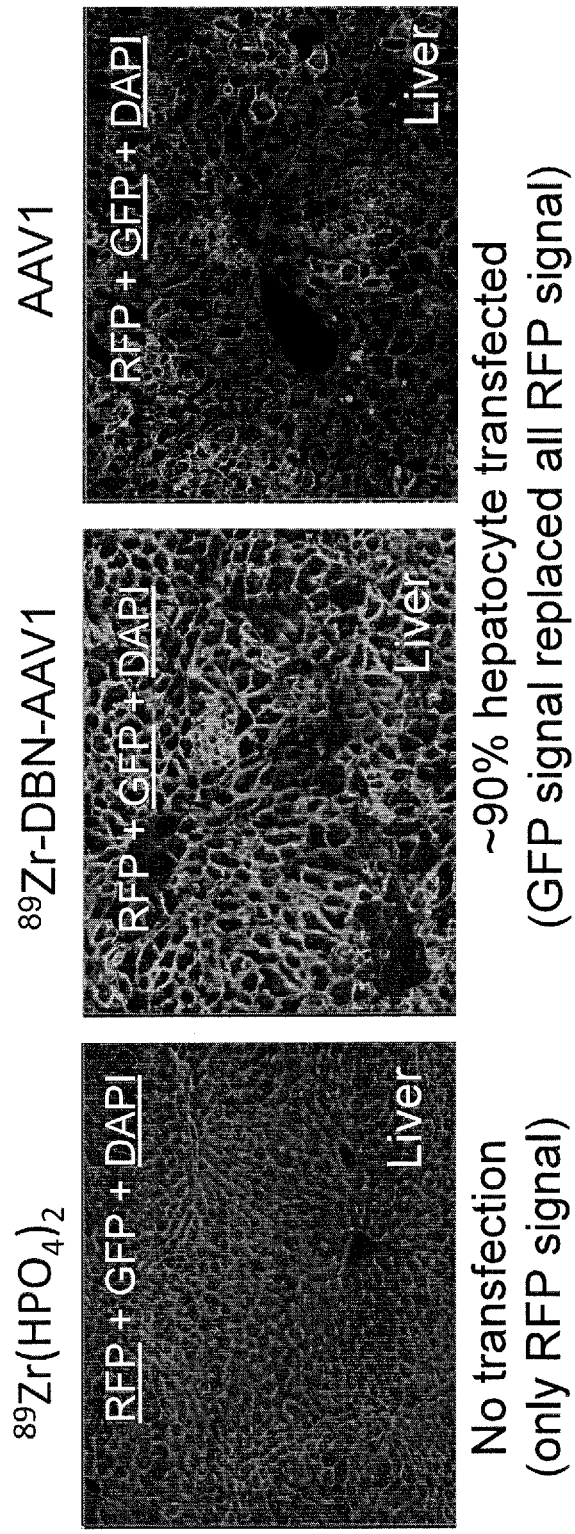
FIG. 11 shows representative fluorescence images of DAPI (4',6-diamidino-2-phenylindole) counter-stained 10µ liver sections confirming transfection. DAPI signal (blue) is showing stained nucleus, GFP signal (green) is showing AAV1 transfected cells and RFP signal (red) is showing untransfected cells.

FIG. 11 shows representative fluorescence images of DAPI counter-stained 10μ liver sections confirming transfection.

Summary $^{89}$Zr(HPO$_4$)$_2$ was readily chelated by DFO-NCS to form $^{89}$Zr-DBN, with radiolabeling efficiency of 55%±5% after 1 hour of reaction.

AAVs were labeled with $^{89}$Zr-DBN and purified using size exclusion PD-10 column.

Radioactivity concentrations of ~20 mCi/10$^{14}$ $^{89}$Zr-DBN-AAVs were achieved after 30 minutes incubation (N=3).

The $^{89}$Zr labeling of AAVs did not affect its viral properties in terms of biodistribution and tissue tropism in a mouse model.

Thus, Example 2 illustrates a novel $^{89}$Zr based virus-labeling method for PET imaging of viral trafficking.

Example 3

In this Example, we report the tracking of transplanted Zirconium-89 ($^{89}$Zr)-labeled mesenchymal stem cells (MSCs) serially with positron emission tomography for 21 days.

Human MSC Preparation: Human MSCs from healthy donors were obtained from the Human Cellular Therapy Laboratory, Mayo Clinic, Rochester, Minn., USA. These cells have been characterized with respect to surface markers. Briefly, they are CD73(+), CD90(+), CD105(+), CD44(+), and HLA-ABC(+), and they are being used in several clinical trials.

Green fluorescent protein (GFP) Transfection: MSCs were transfected with GFP lentivirus from Mayo Clinic Rochester Labs, Rochester, Minn., USA. MSCs were grown overnight in media containing the GFP lentivirus. The medium was changed to complete growth medium the next day, and cells were checked for fluorescence after 48 hours. Once fluorescence was confirmed, the cells were cultured in complete media that contained 1 μg puromycin per milliliter. Cells containing the plasmid were expanded in complete growth media.

$^{89}$Zr Labeling and in Vivo Tracking of Stem Cells: Noninvasive PET imaging was used to evaluate the biodistribution of MSCs delivered to the adventitia outside the arteriovenous fistula (AVF) in CD1-Foxn1nu mice. For this, MSCs were labeled with $^{89}$Zr-DBN. After delivery of 2×10$^5$ 89Zr-labeled MSCs (at a radioactivity concentration of approximately 0.55 MBq per 10$^6$ cells) into the adventitia, the $^{89}$Zr-labeled MSCs were tracked for 3 weeks by using a small-animal PET/radiography system (Genesys4; Sofie BioSystems, Culver City, Calif., USA). In the control group, 0.28 MBq of $^{89}$Zr(HPO$_4$)$_2$ was delivered into the adventitia. PET images were normalized to units of standardized uptake value, which was calculated as follows: tissue radioactivity concentration/(injected dose/body weight in grams).

Figure 12A:
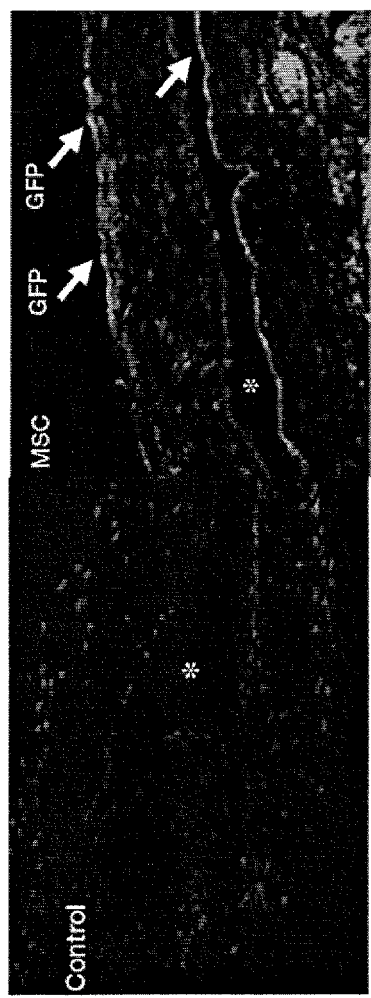
FIG. 12A shows photomicrographs (original magnification, ×20) showing the localization of human adipose tissue-derived mesenchymal stem cells (MSCs). GFP was used to stably transfect 2.5×10$^5$ MSCs, which were injected into the adventitia of the outflow vein of the arteriovenous fistula (AVF) of mice, at the time of creation. GFP-labeled human adipose tissue-derived MSCs are present on day 7 in vessels with transplanted MSCs compared with outflow vein vessels removed from control animals after AVF placement. There are GFP-positive cells (arrows) in the vessel wall of the outflow vein on day 7. *=lumen.
Figure 12B:
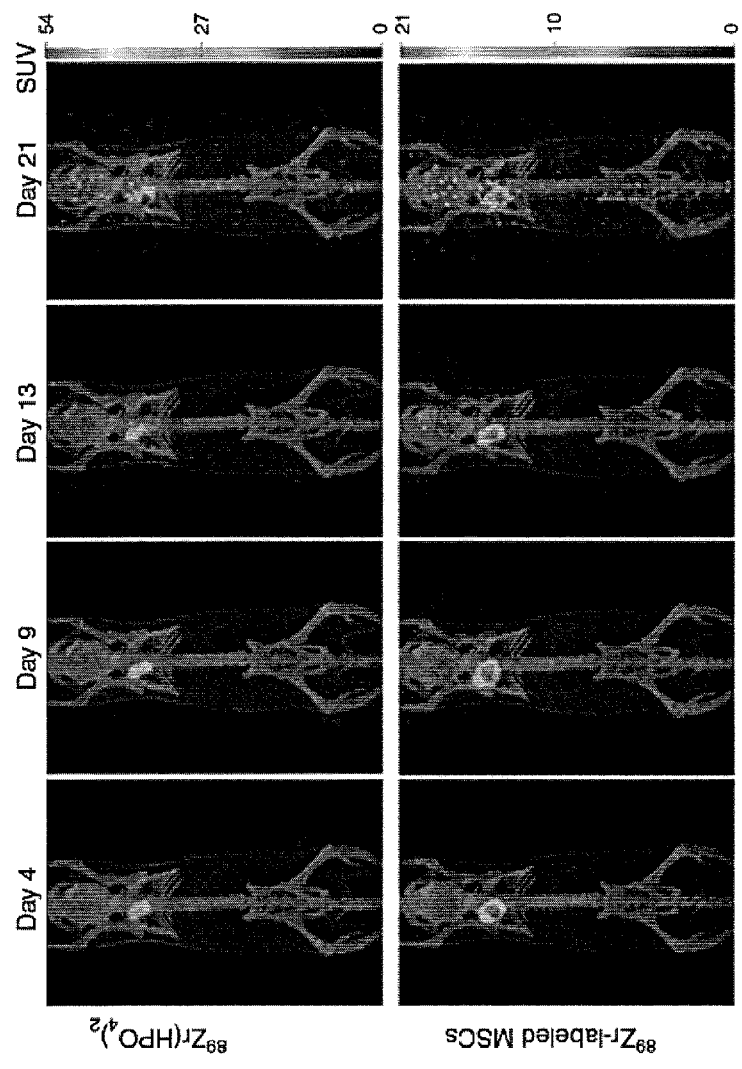
FIG. 12B shows serial PET images of $^{89}$Zr distribution in mice after adventitial delivery of $^{89}$Zr-labeled MSCs or $^{89}$Zr(HPO$_4$)$_2$. The anatomic reference skeleton images are formed by using the mouse atlas registration system algorithm with information obtained from the stationary top-view planar x-ray projector and side-view optical camera.

PET images of mice after adventitial delivery of $^{89}$Zr-labeled MSCs showed that more than 90% of administered $^{89}$Zr radioactivity was retained at the delivery site on day 4 (see FIG. 12A). Adventitial retention of $^{89}$Zr radioactivity cleared slowly from day 4 to day 21, losing approximately 20% over this period (see FIG. 12B). Most $^{89}$Zr radioactivity that was cleared from the adventitia appeared to translocate to bones. This result confirmed results obtained by using confocal microscopy with GFP-labeled cells on day 7. PET imaging of $^{89}$Zr-labeled MSCs allowed tracking of cells beyond 7 days, which was not possible with GFP-labeled cells. The retention of most of the delivered stem cells at the delivery site on day 21 demonstrates that the effect is longer than what was visualized by using GFP labeling. In the case of the control group in which $^{89}$Zr(HPO$_4$)$_2$ was administered, a biodistribution similar to that of $^{89}$Zr-labeled MSCs was seen, with most of the radioactivity (approximately 80%) retained at the delivery site and the rest redistributing to bones.

PET imaging of $^{89}$Zr-labeled MSCs showed most (approximately 80%) of the radiolabel to be retained at the adventitial delivery site, even 3 weeks after delivery. $^{89}$Zr-labeled MSCs delivered intravenously home to the lung, followed by the liver and bones, and free $^{89}$Zr(HPO$_4$)$_2$ is mainly localized in the liver and bones. The use of $^{89}$Zr-labeled MSCs was more sensitive than GFP labeling for detection of cellular location after delivery. Example 3 highlights the fact that MSCs can be tracked after delivery by using PET imaging of $^{89}$Zr-labeled MSCs.

Example 4

Labeling of Viruses with $^{89}$Zr-DBN

A viral suspension in HEPES buffered Hanks Balanced Salt Solution (H-HBSS), pH 7.5-9 (ThermoFisher, Atlanta, Ga., USA) was labeled with $^{89}$Zr-DBN. The AAV labeling reaction was performed with 10$^{10}$-10$^{15}$ viral particles in 500 μl H-HBSS. To this, 100 μl $^{89}$Zr-DBN (~6 MBq) was added and incubated at 37° C. for 10-40 minutes on a shaker. After incubation, the Zr-89 labeled virus was purified from free $^{89}$Zr$^{+4}$ on a PD-10 Sephadex G-25 column.

Figure 13:
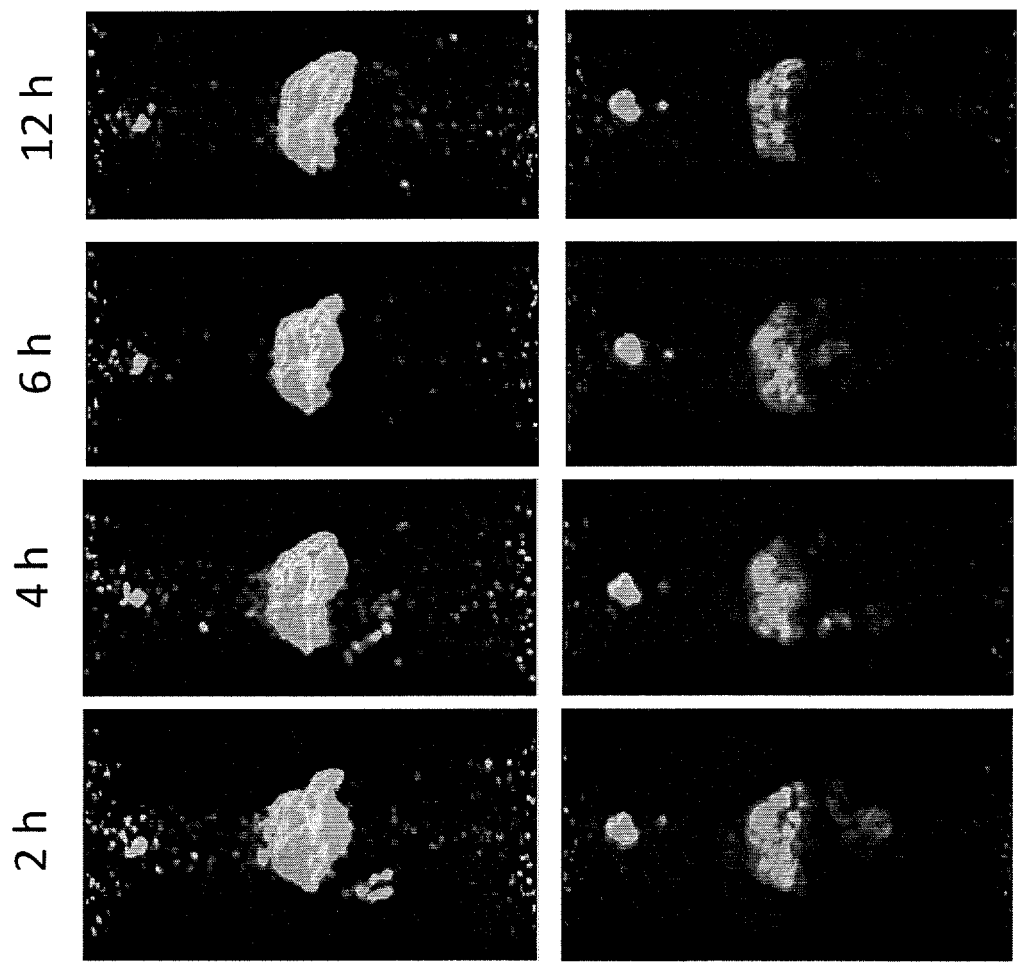
FIG. 13 shows PET images of $^{89}$Zr-labeled AAVs following intravenous delivery in mice.

Adeno-associated virus serotype 8 (AAV8) and adeno-associated virus serotype 9 (AAV9) were labeled with $^{89}$Zr-DBN as above. The in vivo biodistribution of intravenous delivered $^{89}$Zr-DBN-AAV8 and $^{89}$Zr-DBN-AAV9 was assessed by PET imaging and correlated with transfection profile by bio-luminescence imaging in a mouse model system. See FIGS. 13 and 14. Thus, Example 4 illustrates other $^{89}$Zr based virus-labeling methods for PET imaging of viral trafficking.

List of abbreviations used herein:
$^{89}$Zr(HPO$_4$)$_2$: Zirconium hydrogen phosphate
AAV: adeno-associated virus
Alpha MEM: Alpha Modified Eagle's Medium
Anti-CD45: antibody against cluster of differentiation-45 antigen
DBN: desferrioxamine-NCS
DFO-Bz-NCS: Desferrioxamine-Benzyl-Sodium thiocyanate
DMEM: Dulbecco's Modified Eagle's Medium
DTPA: Diethylene triamine pentaacetic acid
FBS: Fetal Bovine Serum
FDG: $^{18}$F-2-fluoro-2-deoxy-D-glucose
GFP: Green fluorescent protein
GM-CSF: Granulocyte-macrophage colony-stimulating factor
HBSS: Hank's Balanced Salt Solution
HEPES-KOH: (4-(2-hydroxyethyl)-1-piperazineethanesulfonic acid)-Potassium hydroxide
HMPAO: hexamethylpropyleneamine oxime
hMSCs: human mesenchymal stem cells
IgG: immunoglobulin G
IgM: immunoglobulin M
iTLC: instant thin layer chromatography
K$_2$CO$_3$: Potassium carbonate
K$_2$HPO$_4$/KH$_2$PO$_4$: dipotassium hydrogen phosphate/potassium hydrogen phosphate
MBq: Mega Becquerel
mDCs: mouse derived dendritic cells
MIPs: maximal images projection
mMCs: mouse derived melanoma cells
PET: Positron Emission Tomography
PTSM: Pyruvaldehyde-bis(N4-methylthiosemicarbazone)
Rf: Retention factor
SPECT: single-photon emission computerized tomography
T$_{1/2}$: Half-life of radioisotope

REFERENCES

1. Nguyen P K, Riegler J, Wu J C. Stem cell imaging: from bench to bedside. Cell stem cell. 2014; 14:431-44.
2. Gildehaus F J, Haasters F, Drosse I, Wagner E, Zach C, Mutschler W, et al. Impact of indium-111 oxine labelling on viability of human mesenchymal stem cells in vitro, and 3D cell-tracking using SPECT/CT in vivo. Mol Imaging Biol. 2011; 13:1204-14.
3. Hughes D K. Nuclear medicine and infection detection: the relative effectiveness of imaging with $^{111}$In-oxine-, $^{99m}$Tc-HMPAO-, and $^{99m}$Tc-stannous fluoride colloid-labeled leukocytes and with $^{67}$Ga-citrate. J Nucl Med Tech. 2003; 31:196-201.
4. Brenner W, Aicher A, Eckey T, Massoudi S, Zuhayra M, Koehl U, et al. 111In-labeled CD34+ hematopoietic progenitor cells in a rat myocardial infarction model. J Nucl Med. 2004; 45:512-8.
5. Kuyama J, McCormack A, George A J, Heelan B T, Osman S, Batchelor J R, et al. Indium-111 labelled lymphocytes: isotope distribution and cell division. Eur J Nucl Med. 1997; 24:488-96.
6. Roca M, de Vries E F, Jamar F, Israel O, Signore A. Guidelines for the labelling of leucocytes with $^{(111)}$In-oxine. Inflammation/Infection Taskgroup of the European Association of Nuclear Medicine. Eur J Nucl Med Mol Imaging. 2010; 37:835-41.
7. Adonai N, Nguyen K N, Walsh J, Iyer M, Toyokuni T, Phelps M E, et al. Ex vivo cell labeling with $^{64}$Cu-pyruvaldehyde-bis(N4-methylthiosemicarbazone) for imaging cell trafficking in mice with positron-emission tomography. Proc Nat Acad Sci. 2002; 99:3030-5.
8. Tarantal A F, Lee C C, Kukis D L, Cherry S R. Radiolabeling human peripheral blood stem cells for positron emission tomography (PET) imaging in young rhesus monkeys. PloS one. 2013; 8:e77148.
9. Charoenphun P, Meszaros L K, Chuamsaamarkkee K, Sharif-Paghaleh E, Ballinger J R, Ferris T J, et al. [$^{89}$Zr] Oxinate for long-term in vivo cell tracking by positron emission tomography. Eur J Nucl Med Mol Imaging. 2014. [Epub ahead of print]
10. Davidson-Moncada J, Sato N, Hoyt Jr, et al. A novel method to study the in vivo trafficking and homing of adoptively transferred NK cells in Rhesus Macaques and Humans. Proceedings of the 56th Annual Meeting of the American Society of Hematology, San Francisco, Calif., Dec. 6-9, 2014. Abstract #659.
11. Sato N, S. L., Choyke P, Cell labeling using Zr-89—comparison with In-111 oxine. Proceedings World Molecular Imaging Congress, Savannah, G A, 2013, 2013: p. P533.
12. Stojanov K, de Vries E F, Hoekstra D, van Waarde A, Dierckx R A, Zuhorn I S. [$^{18}$F]FDG labeling of neural stem cells for in vivo cell tracking with positron emission tomography: inhibition of tracer release by phloretin. Mol Imaging. 2012; 11:1-12.
13. Zhang Y, Dasilva J N, Hadizad T, Thorn S, Kuraitis D, Renaud J M, et al. $^{18}$F-FDG cell labeling may underestimate transplanted cell homing: more accurate, efficient, and stable cell labeling with hexadecyl-4-[$^{18}$F]fluorobenzoate for in vivo tracking of transplanted human progenitor cells by positron emission tomography. Cell Transplant. 2012; 21:1821-35.
14. Meier R, Piert M, Piontek G, Rudelius M, Oostendorp R A, Senekowitsch-Schmidtke R, et al. Tracking of [$^{18}$F] FDG-labeled natural killer cells to HER2/neu-positive tumors. Nucl Med Biol. 2008; 35:579-88.
15. Doyle B, Kemp B J, Chareonthaitawee P, Reed C, Schmeckpeper J, Sorajja P, et al. Dynamic tracking during intracoronary injection of $^{18}$F-FDG-labeled progenitor cell therapy for acute myocardial infarction. J Nucl Med. 2007; 48:1708-14.
16. Pellegrino D, Bonab A A, Dragotakes S C, Pitman J T, Mariani G, Carter E A. Inflammation and infection: imaging properties of $^{18}$F-FDG-labeled white blood cells versus $^{18}$F-FDG. J Nucl Med. 2005; 46:1522-30.
17. de Vries E F, Roca M, Jamar F, Israel O, Signore A. Guidelines for the labelling of leucocytes with $^{99m}$Tc-HMPAO. Inflammation/Infection Taskgroup of the European Association of Nuclear Medicine. Eur J Nucl Med Mol Imaging. 2010; 37:842-8.
18. Pandey M K, Engelbrecht H P, Byrne J P, Packard A B, DeGrado T R. Production of $^{89}$Zr via the $^{89}$Y(p,n)$^{89}$Zr reaction in aqueous solution: effect of solution composition on in-target chemistry. Nucl Med Biol. 2014; 41:309-16.
19. Holland J P, Sheh Y, Lewis J S. Standardized methods for the production of high specific-activity Zirconium-89. Nucl Med Biol. 2009; 36:729-39.
20. Naumova A V, Modo M, Moore A, Murry C E, Frank J A. Clinical imaging in regenerative medicine. Nat Biotech. 2014; 32:804-18.
21. Glaudemans A W, Galli F, Pacilio M, Signore A. Leukocyte and bacteria imaging in prosthetic joint infection. Eur Cell Mater. 2013; 25:61-77.
22. Kassis A I, Adelstein S J. Chemotoxicity of indium-111 oxine in mammalian cells. J Nucl Med. 1985; 26:187-90.
23. Holland J P, Divilov V, Bander N H, Smith-Jones P M, Larson S M, Lewis J S. $^{89}$Zr-DFO-J591 for immunoPET of prostate-specific membrane antigen expression in vivo. J Nucl Med. 2010; 51:1293-300.
24. Keberle H. The Biochemistry of Desferrioxamine and Its Relation to Iron Metabolism. Annals N Y Acad Sci. 1964; 119:758-68.
25. Takagai Y, Takahashi A, Yamaguchi H, Kubota T, Igarashi S. Adsorption behaviors of high-valence metal ions on desferrioxamine B immobilization nylon 6,6 chelate fiber under highly acidic conditions. J Colloid Interface Sci. 2007; 313:359-62.
26. Deri M A, Zeglis B M, Francesconi L C, Lewis J S. PET imaging with $^{89}$Zr: from radiochemistry to the clinic. Nucl Med Biol. 2013; 40:3-14.
27. Vosjan M J, Perk L R, Visser G W, Budde M, Jurek P, Kiefer G E, et al. Conjugation and radiolabeling of monoclonal antibodies with Zirconium-89 for PET imaging using the bifunctional chelate p-isothiocyanatobenzyl-desferrioxamine. Nat Protoc. 2010; 5:739-43.
28. Perk L R, Vosjan M J, Visser G W, Budde M, Jurek P, Kiefer G E, et al. p-Isothiocyanatobenzyl-desferrioxamine: a new bifunctional chelate for facile radiolabeling of monoclonal antibodies with Zirconium-89 for immuno-PET imaging. Eur J Nucl Med Mol Imaging. 2010; 37:250-9.
29. Dijkers E C F, Kosterink J G W, Rademaker A P, Perk L R, van Dongen GAMS, Bart J, et al. Development and characterization of clinical-grade Zr-89-trastuzumab for HER2/neu immunoPET imaging. J Nucl Med. 2009; 50:974-81.
30. Schrepfer S, Deuse T, Reichenspurner H, Fischbein M P, Robbins R C, Pelletier M R Stem cell transplantation: the lung barrier. Transplant Proc. 2007; 39:573-6.
31. Fischer U M, Harting M T, Jimenez F, Monzon-Posadas W O, Xue H, Savitz S I, et al. Pulmonary passage is a major obstacle for intravenous stem cell delivery: the pulmonary first-pass effect. Stem Cells Dev. 2009; 18:683-92.
32. Gao J, J E Dennis, R F Muzic, M Lundberg and A I Caplan. The dynamic in vivo distribution of bone marrow-derived mesenchymal stem cells after infusion. Cells Tissues Organs 2001; 169:12-20.
33. Daldrup-Link H E, M Rudelius, S Metz, G Piontek, B Pichler, M Settles, U Heinzmann, J Schlegel, R A Oostendorp and E J Rummeny. Cell tracking with gadophrin-2: a bifunctional contrast agent for MR imaging, optical imaging, and fluorescence microscopy. Eur J Nucl Med Mol Imaging 2004; 31:1312-21.
34. Terrovitis J, Lautamaki R, Bonios M, Fox J, Engles J M, Yu J, et al. Noninvasive quantification and optimization of acute cell retention by in vivo positron emission tomography after intramyocardial cardiac-derived stem cell delivery. J Am Coll Cardiol. 2009; 54:1619-26.
35. Boerjesson P K E, Jauw Y W S, de Bree R, Roos J C, Castelijns J A, Leemans C R, et al. Radiation dosimetry of Zr-89-labeled chimeric monoclonal antibody U36 as used for immuno-PET in head and neck cancer patients. J Nucl Med. 2009; 50:1828-36.
36. Borjesson P K E, Jauw Y W S, Boellaard R, de Bree R, Comans E F I, Roos J C, et al. Performance of immuno-positron emission tomography with Zirconium-89-labeled chimeric monoclonal antibody U36 in the detection of lymph node metastases in head and neck cancer patients. Clin Cancer Res. 2006; 12:2133-40.
37. Rizvi S N F, Visser O J, Vosjan M J W D, van Lingen A, Hoekstra O S, Zijlstra J M, et al. Biodistribution, radiation dosimetry and scouting of Y-90-ibritumomab tiuxetan therapy in patients with relapsed B-cell non-Hodgkin's lymphoma using Zr-89-ibritumomab tiuxetan and PET. Eur J Nucl Med Mol Imaging. 2012; 39:512-20.
38. Dijkers E C, Munnink T H O, Kosterink J G, Brouwers A H, Jager P L, de Jong J R, et al. Biodistribution of Zr-89-trastuzumab and PET imaging of HER2-positive lesions in patients with metastatic breast cancer. Clin Pharmacol Ther. 2010; 87:586-92.
39. S. B. M. Gaykema, A. H. Brouwers, M. N. L. Hooge et al. $^{89}$Zr-bevacizumab PET imaging in primary breast cancer. J Nucl Med. 2013; 54: 1014-18.
40. Deri M A, Ponnala S, Zeglis B M, Pohl G, Dannenberg J J, Lewis J S, Francesconi L C. Alternative chelator for $^{89}$Zr radiopharmaceuticals: radiolabeling and evaluation of 3,4,3-(LI-1,2-HOPO). J Med Chem. 2014; 57:4849-60.
41. Yang B, Brahmbhatt A, Nieves Torres E, Thielen B, McCall D L, Engel S, Bansal A, Pandey M K, Dietz A B, Leof E B, DeGrado T R, Mukhopadhyay D, Misra S., "Tracking and Therapeutic Value of Human Adipose Tissue-derived Mesenchymal Stem Cell Transplantation in Reducing Venous Neointimal Hyperplasia Associated with Arteriovenous Fistula", Radiology. 2015 Nov. 19:150947.

The citation of any document or reference is not to be construed as an admission that it is prior art with respect to the present invention.

Thus, the invention provides methods of ex vivo labeling of a biological material for in vivo imaging, methods of labeling a biological material in vivo, methods for preparing a labeling agent, and methods for in vivo imaging of a subject using a biological material labeled with a labeling agent. In one non-limiting example, the biological material is selected from cells.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A biological material selected from stem cells, the biological material being labeled with a labeling agent comprising:
   a chelating moiety, a conjugation moiety, and at least one of (i) a radionuclide and (ii) a paramagnetic metal ion or compound,
   wherein the chelating moiety includes a hydroxamic acid group and the conjugation moiety includes an isothiocyanate group, and
   wherein the isothiocyanate group of the labeling agent binds to the biological material.
2. The biological material of claim 1 wherein:
   the hydroxamic acid group is a desferrioxamine group.
3. The biological material of claim 1 wherein:
   the conjugation moiety includes a benzyl group.
4. The biological material of claim 1 wherein:
   the labeling agent comprises a radionuclide, and
   the radionuclide is selected from the group consisting of $^{11}$C, $^{13}$N, $^{15}$O, $^{18}$F, $^{34m}$Cl, $^{38}$K, $^{45}$Ti, $^{51}$Mn, $^{52}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{99m}$Tc, $^{110m}$In, $^{111}$In, $^{118}$Sb, $^{120}$I, $^{121}$I, $^{122}$I, $^{123}$I, and $^{124}$I.
5. The biological material of claim 1 wherein:
   the labeling agent comprises a radionuclide, and
   the radionuclide is a positron emitter.
6. The biological material of claim 5 wherein:
   the positron emitter is $^{89}$Zr.
7. The biological material of claim 1 wherein:
   the labeling agent comprises a paramagnetic metal ion.
8. The biological material of claim 7 wherein:
   the paramagnetic metal ion is selected from the group consisting of $Gd^{+3}$, $Fe^{+3}$, $Mn^{+2}$, and $Y^{+3}$.
9. The biological material of claim 1 wherein:
   the labeling agent comprises a paramagnetic compound, and
   the paramagnetic compound includes one or more $^{19}$F atoms.
10. The biological material of claim 1 wherein:
    the biological material is suitable for labeling in a time period of 10-40 minutes.
11. The biological material of claim 10 wherein:
    the biological material is suitable for labeling at a pH range of 7.5-9.
12. The biological material of claim 11 wherein:
    the biological material is suitable for labeling at pH 7.5.
13. The biological material of claim 1, the chelating moiety includes three hydroxamate groups.
14. The biological material of claim 13, wherein the labeled biological material includes a radionuclide, and retention of radioactivity is stable for at least 1 day.
15. The biological material of claim 13, wherein the labeled biological material includes a radionuclide, and retention of radioactivity is stable for at least 4 days.
16. The biological material of claim 13, wherein the labeled biological material includes a radionuclide, and retention of radioactivity is stable for at least 7 days.
17. The biological material of claim 1 wherein:
    the hydroxamic acid group is a desferrioxamine group,
    the conjugation moiety includes a benzyl group, and
    the labeling agent comprises $^{89}$Zr.

* * * * *

UNITED STATES PATENT AND TRADEMARK OFFICE
CERTIFICATE OF CORRECTION

PATENT NO. : 11,534,506 B2
APPLICATION NO. : 15/555775
DATED : December 27, 2022
INVENTOR(S) : Aditya Bansal et al.

It is certified that error appears in the above-identified patent and that said Letters Patent is hereby corrected as shown below:

In the Specification

Column 18, Line 9, "FVB.129S6(136)" should be --FVB.129S6(B6)--.

Signed and Sealed this
Twenty-eighth Day of February, 2023

Katherine Kelly Vidal
*Director of the United States Patent and Trademark Office*